(12) United States Patent
Snyder et al.

(10) Patent No.: US 6,797,505 B2
(45) Date of Patent: Sep. 28, 2004

(54) RECOMBINANT AAV VECTORS FOR GENE THERAPY OF HEMOPHILIA A

(75) Inventors: Richard O. Snyder, Oakland, CA (US); Thomas J. Dull, San Francisco, CA (US); Ryan McGuinness, Half Moon Bay, CA (US); Mitchell H. Finer, Woodside, CA (US)

(73) Assignee: Cell Genesys, Inc., South San Francisco, CA (US)

( * ) Notice: Subject to any disclaimer, the term of this patent is extended or adjusted under 35 U.S.C. 154(b) by 0 days.

(21) Appl. No.: 09/084,425

(22) Filed: May 27, 1998

(65) Prior Publication Data

US 2002/0155580 A1 Oct. 24, 2002

(51) Int. Cl.$^7$ ................................................ C12N 7/01
(52) U.S. Cl. ...................................... 435/235.1; 514/44
(58) Field of Search ........................... 435/235.1; 514/44

(56) References Cited

U.S. PATENT DOCUMENTS

| | | | |
|---|---|---|---|
| 5,139,941 A | | 8/1992 | Muzyczka et al. |
| 5,866,552 A | * | 2/1999 | Wilson et al. ................ 514/44 |
| 6,093,392 A | * | 7/2000 | High et al. ............... 435/230.1 |
| 6,200,560 B1 | * | 3/2001 | Couto et al. ............... 424/93.2 |
| 6,221,349 B1 | * | 4/2001 | Couto et al. ............... 424/93.2 |
| 6,268,213 B1 | | 7/2001 | Samulski et al. |

FOREIGN PATENT DOCUMENTS

| | | |
|---|---|---|
| EP | 0 786 474 A1 | 6/1990 |
| WO | WO 98/09524 | 12/1998 |

OTHER PUBLICATIONS

Sokol et al., "Human Genone—Chromosome No. 19" Cas. Lek. Ces., 134(19):625–629 (1995).

Su et al., "Selective Killing of AFP–Positive Hepatocellular Carcinoma Cells by Adeno–Associated Virus Transfer of the Herpes Simplex Virus Thymidine Kinase Gene" Human Gene Therapy 7:463–470 (1996).

Wang et al., "Rescue and Replication of Adeno–Associated Virus Type 2 as well as Vector DNA Sequences from Recombinant Plasmids Containing Deletions in the Viral Inverted Terminal Repeats: Selective Encapsidation of Viral Genomes in Progeny Virions" J. Virology, 70(3):1668–1677 (1996).

Wang et al., "Rescue and Replication Signals of the Adeno–associated Virus 2 Genome", J. Mol. Biol. 250:573–580. (1995).

Kotin, "Prospects for the Use of . . . Gene Therapy", Hum. Gene Ther. 5:793–801 (1994).

Koberl et al., "Transduction of hepatocytes in vivo with adeno–associated virus vectors as a model for hepatic gene therapy"Am. J. of Human Genetic 57:218 (1995).

Robert M. Kotin, "Prospects for the Use of Adeno–Associated Virus as a Vector for Human Gene Therapy" Human Gene 5:793–801 (1994).

Ponnazhagan et al., "Adeno–Associated Virus 2–Mediated Gene Transfer and Expression in Murine Hematopoietic Progenitor Cells in Vivo" Blood, 10: 948 (1995).

Charles R. III et al., "Optimization of human factor VIII . . . hemophilia A" *Blood Coagulation and Fibrinolysis* 8(2):S23–S30, 1997.

Salier et al., "Functional Characterization . . . Factor IX Gene" *J. Biolo. Chem.* 265(12):7062–7068, 1990.

Lind et al., "Novel forms of . . . biochemical characterization" *Eur. J. Biochem.* 232:19–27, 1995.

Pittman et al., "Biochemical, immunological, . . . Factor VIII" *Blood* 81(11):2925–2935, 1993.

Mikkelsen et al. "Expression of a cytomegalovirus . . . transgenic mice" *Transgenic Res.* 1:164–169, 1992.

Herzog et al., Stable gene transfer and expression of human blood coagulation factor IX after intramuscular infection of recombinant adeno–associated virus. Proc. Natl. Acad. Sci. USA 94:5804–5809, May 27, 1997.*

* cited by examiner

*Primary Examiner*—James Housel
*Assistant Examiner*—Stacy B. Chen
(74) *Attorney, Agent, or Firm*—Linda Judge; Piper Rudnick, LLP

(57) ABSTRACT

The instant invention provides methods and materials for expressing a polypeptide with factor VIII activity comprising administering an rAAV vector encoding a truncated version of human factor VIII, containing, for example, a 90 kD heavy chain of factor VIII fused to a light chain of factor VIII.

20 Claims, 14 Drawing Sheets

RECOMBINANT AAV VECTORS FOR GENE THERAPY OF HEMOPHILIA A

BACKGROUND OF THE INVENTION

I. Adeno-Associated Virus

Adeno-associated virus (AAV) is a defective parvovirus whose genome is encapsidated as a single-stranded DNA molecule. Strands of plus and minus polarity are packaged with equal efficiency, but in separate virus particles. Efficient replication of AAV generally requires coinfection with a helper virus of the herpesvirus or adenovirus family, although under special circumstances, AAV can replicate in the absence of helper virus.

In the absence of helper virus, AAV establishes a latent infection in which the viral genome exists as an integrated provirus in the host cell. Integration of the virus occurs on human chromosome 19. If a latently infected cell line later is superinfected with a suitable helper virus, generally the AAV provirus is excised and the AAV virus enters the "productive" phase.

AAV isolates have been obtained from human and simians. The host range for lytic growth of AAV is broad. Cell lines from virtually every mammalian species tested, including a variety of human, simian, canine, bovine and rodent cell lines, can be infected productively with AAV, provided an appropriate helper virus is used (e.g., canine adenovirus in canine cells). However, no disease has been associated with AAV in either human or other animal populations.

AAV has been isolated as a nonpathogenic coinfecting agent from fecal, ocular and respiratory specimens during acute adenovirus infection, but not during other illnesses. Latent AAV infections have been identified in both human and nonhuman cells. Overall, virus integration appears to have no apparent effect on cell growth or morphology, see Samulski, Curr. Op. Gen. Devel., 3:74–80 (1993).

There are a number of AAV's, including AAV-1, AAV-2, AAV-3, AAV-4 and AAV-5. The genome of AAV-2 is 4,679 bases in length (Genbank No. AF043303) and contains inverted terminal repeat sequences of 145 bases each. The repeats are believed to act as origins of DNA replication. The AAV-3 genome is 4726 bases in length and has 82% overall sequence homology with AAV-2, see Muramatsu, Virology, 221:208–217 (1996). Like AAV-2, both ends of the AAV-3 genome consist of inverted repeats but the palindromes are 146 bp in size. Certain portions of the AAV-2 and AAV-3 genomes are highly conserved, for example, there are two sites in the hairpin where there is only a single base pair substitution between AAV-2 and AAV-3.

The AAV genome has two major open reading frames. The left frame encodes at least four non-structural proteins (the Rep group). There are two promoters, P5 and P19, which control expression of those proteins. As a result of differential splicing, the P5 promoter directs production of proteins Rep 78 and Rep 68, and the P19 promoter, of the proteins Rep 52 and Rep 40. The Rep proteins are believed to be involved in viral DNA replication, trans-activation of transcription from the viral promoters, repression of heterologous enhancers and promoters as well as with site-specific integration.

The right ORF, controlled by the P40 promoter, encodes the capsid proteins, Vp1 (91 kDa), Vp2 (72 kDa) and Vp3 (60 kDa). Vp3 comprises 80% of the virion structure while Vp1 and Vp2 are minor components. There is a polyadenylation site at map unit 95. For the complete sequence of the AAV-2 genome, see Strivastava et al., J. Virol., 45:555–64 (1983).

McLaughlin et al., J. Virol., 62:1963–73 (1988) prepared two AAV vectors: dl 52–91, which retains the AAV rep genes, and dl 3–94 in which all of the AAV coding sequences are deleted. dl 3–94 does, however, retain the two 145 base terminal repeats and an additional 139 bases which contain the AAV polyadenylation signal. A foreign gene, encoding neomycin resistance, was inserted into the vector. Viral stocks were prepared by complementation with a recombinant AAV genome which supplied the missing AAV gene products in trans but was itself too large to be packaged. Unfortunately, the virus stocks were contaminated with wild type AAV (10% in the case of dl 3–94) presumably as a result of homologous recombination between the defective and the complementing viruses.

Samulski et al., J. Virol., 63:3822–28 (1989) developed a method of producing recombinant AAV stocks without detectable wild-type helper AAV. The AAV vector retained only the terminal 191 bases of the AAV chromosome. In the AAV helper plasmid (pAAV/Ad), the terminal 191 bases of the AAV chromosome were replaced with adenovirus terminal sequences. Since sequence homology between the vector and the helper AAV thus essentially was eliminated, no detectable wild-type AAV was generated by homologous recombination. Moreover, the helper DNA itself was not replicated and encapsidated because the AAV termini are required for that process. Thus, in the AAV system, unlike the HSV system, helper virus could be eliminated completely leaving a helper-free AAV vector stock.

Recombinant AAV (rAAV) vectors have been used for expressing gene products in animals, see, for example, U.S. Pat. No. 5,193,941 and WO 94/13788. Other patents and publications describe AAV vectors and uses, the uses generally being related to expression of gene products either in vitro (usually tissue cultures) or in vivo (usually in the lungs or oral mucosa, the normal sites of AAV infection, but expression in other tissues, such as the central nervous system and in cardiac tissue has been observed).

Transduction of rAAV vectors harboring the bacterial β-galactosidase gene by single injection into the quadriceps of mice demonstrated that expression was maintained long-term and the expression did not decrease substantially during that time (Xiao et al., J. Virol., 70:8098–8108 (1996)). Other targets successfully transduced with rAAV vectors include: T-lymphocytes and B-lymphocytes, human erythroleukemia cells, different regions of the rat brain, the striatum of the rat brain in a Parkinson's Disease model with the tyrosine hydroxylase gene, heart of the pig and rat with the LacZ gene, the peripheral auditory system of the guinea pig and bronchial epithelia of the rabbit and monkey. In addition, a Phase I human clinical trial for the delivery of an rAAV-CFTR vector is in progress.

AAV's harboring the human factor IX gene were infused into the portal vein of adult immunocompetent mice and long-term gene expression was obtained (Snyder et al., Nat. Genet., 16:270–276 (1997)). The vectors were found to be integrated into the murine genome (Miao et al., Nat. Genet., 19:13–15 (1998)).

II. Hemophilia

Hemophilia A is an X chromosome-linked bleeding disorder resulting from a deficiency of or an abnormality of factor VIII (FVIII or fVIII), a component of the coagulation cascade. The human FVIII cDNA has been cloned. FVIII is synthesized as a 2351 amino acid residue, single chain precursor composed of a 19 amino acid signal peptide and six distinct domains. The domains are arranged in the order, A1-A2-B-A3-C1-C2 (Toole et al., Nature, 312:342–347 (1984); Vehar et al., Nature, 312:337–342 (1984)). An A domain contains about 330 amino acids and is present in three copies. A C domain contains about 150 amino acids and is present in two copies. The B domain contains about 909 amino acids and is extremely rich in potential N-linked glycosylation sites.

The translation product of the FVIII gene first is cleaved between the B domain and the A3 domain. Then, the B domain is proteolysed at multiple sites leaving FVIII as a divalent metal ion-linked complex consisting of the heavy chain (H chain) of 90–200 kDa and the light chain (L chain) of 80 kDa (Vehar et al., (1984), supra; Anderson et al., Proc. Natl. Acad. Sci. USA, 83:2979–2983 (1986)).

The minimal functional unit of FVIII is the heterodimer consisting of the 90 kDa H chain and the 80 kDa L chain. Thus, the B domain is dispensable for procoagulant activity (Eaton et al., Biochemistry, 25:8343–8347 (1986); Toole et al., Proc. Natl. Acad. Sci., USA 83:5939–5942 (1986)). Circulating FVIII in blood is associated with the von Willebrand factor (vWF) which is a large multimeric, multifunctional product (Brinkhous et al., Proc. Natl. Acad. Sci. USA, 82:8752–8756 (1985)).

Hemophilia A patients are at risk of contracting transmissible infectious diseases from plasma-derived FVIII used in treatment. Thus, recombinant product is a desirable alternative. However, the complicated processing and large size of FVIII have hampered production of FVIII in prokaryotes or lower eukaryotes.

Expression of full-length FVIII cDNA in mammalian cells was reported by several groups, but the levels of expression were very low and insufficient for economical production of recombinant FVIII (rFVIII).

To improve expression efficiency, modified FVIII cDNA's lacking most of the B domain were made (Eaton et al., (1986), supra; Toole et al., (1986), supra; Sarver et al., Behring Inst. Mitt., 82:16–25 (1988); Meulien et al., Protein Engng., 2:301–306 (1988); Tajima et al., Proc. 6th Int. Symp., II.T:51–63 (1990)) and the resulting products were shown to retain functional activities of FVIII.

Tajima et al., (1990), supra, fused the coding sequences of the H and L chains. Although that construct was expressed about 10-fold higher than a full length FVIII cDNA construct, 20% of the product was not cleaved to the H and L chains or was cleaved incorrectly. Eaton et al. ((1986), supra) inserted a junction peptide derived from the B-domain between the H and L chains. However, the junction peptide remained at the C terminus of the H chain. Such fusion molecules have antigenic properties (Esmon et al., Blood, 76:1593–1600 (1990)) which can elicit serious side effects because of the constant exposure of the host to those antigens during the extended duration of treatment.

Burke et al. (J. Biol. Chem. 261:12574–12578 (1986)) expressed the H chain (Ala1-Arg740) and the L chain (Glu1649-Tyr2332) as separate proteins in COS cells and observed secretion of functionally active FVIII. But the expression levels were even lower than that of the full length construct. Yonemura et al. (Prot. Engng., 6:669–674 (1993)) essentially duplicated those efforts using plasmids in CHO cells.

Another complication of the disease is the observation that the severity of the bleeding tendency varies among patients and may be related to the concentration of functional clotting factors. Individuals can have mild hemophilia that may not be recognized until adulthood or following heavy trauma or surgery, see, for example, Reiner & Davie, "Introduction to hemostasis and the vitamin K-dependent coagulation factors" in *The Metabolic Basis of Inherited Disease* (Scriver et al., eds.) Vol. 3, pages 3181–3221 (McGraw Hill, N.Y., 1995).

III. Therapy

Adenovirus vectors can infect non-dividing cells and therefore, can be delivered directly into mature tissue, such as muscle. However, the transgenes delivered by adenovirus vectors are not useful for long term expression for a variety of reasons. First, adenovirus vectors retain most of the viral genes and thus pose potential problems, i.e. safety. Expression of the adenovirus genes can cause the immune system to destroy the cells containing the vectors (see, for example, Yang et al., Proc. Natl. Acad. Sci. 91:4407–4411 (1994)). Since adenovirus is not an integration virus, the vector eventually will be diluted or degraded in the cells. Also, because of the immune response, adenovirus vectors cannot be delivered repeatedly. In the case of lifetime disease, such as the hemophilias, that will be a major limitation.

For retrovirus vectors, although stable integration into the host chromosomes can be achieved, the use thereof is restricted because currently used vectors only can infect dividing cells, a large majority of target cells being non-dividing.

AAV vectors have certain advantages over the above-mentioned vector systems. First, like adenovirus, AAV infects non-dividing cells. Second, all the AAV viral genes are eliminated in the vector. Since the viral gene expression-induced immune reaction is no longer a concern, AAV vectors are safer than adenovirus vectors. As AAV is an integration virus, integration into the host chromosome will maintain the transgene in the cells. AAV is an extremely stable virus, resistant to many detergents, pH changes and heat (stable at 56° C. for about an hour). AAV can be lyophilized and redissolved without losing significant activity. Finally, AAV causes no known diseases or pathogenic symptoms in humans. Therefore, AAV is a very promising delivery vehicle for gene therapy.

Two recent review articles provide an overview of the recent status on the use of AAV vectors and include a collection of additional recent scientific publications in the field: Samulski, "Adeno-associated Viral Vectors", Chap. 3 in "Viruses in Human Gene Therapy", Vos et al., ed., Chapman & Hall, 1994; and Samulski, "Adeno-associated Virus-based Vectors for Human Gene Therapy", Chap. 11 in "Gene Therapy: From Laboratory to the Clinic", Hui et al., ed., World Scientific, 1994.

Since AAV has in the past been shown to have a broad host range; can be administered by a variety of routes, including intramuscular injection; and is operable in different cells types, such as liver, retina, neurons and so on, there are no known limits of the host in which the herein described methods of delivery can take place, particularly in, for example, mammals and birds, especially domesticated mammals and birds, such as cattle, sheep, pigs, horses, dogs, cats, chickens and turkeys. Both human and veterinary uses particularly are preferred.

SUMMARY OF THE INVENTION

The instant invention provides recombinant AAV vectors for effective expression of a protein with Factor VIII function to treat hemophilia A and homologous disorders. The recombinant AAV vectors described herein provide a significant development in the field of recombinant AAV vector gene therapy.

The rAAV vectors of the invention can be used as viral particles alone. Alternatively, the rAAV vector virus particles can be used in conjunction with additional treatments, including partial hepatectomy or treatment with secondary agents that enhance transduction, whether associated with in vivo or ex vivo therapies. Examples of secondary agents include gamma irradiation, UV irradiation, tritiated nucleotides such as thymidine, cis-platinum, etoposide, hydroxyurea, aphidicolin and adenovirus.

DESCRIPTION OF SPECIFIC EMBODIMENTS

Figure 1:
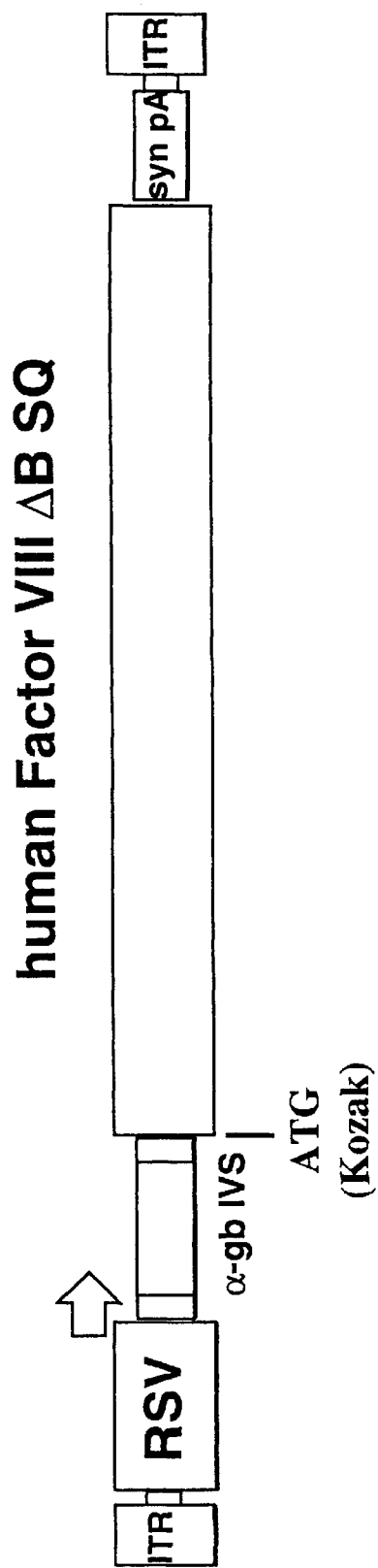
FIG. 1 is a schematic representation of the rAAV-RSV-human-Factor VIII vector. ITR:AAV inverted terminal repeat; RSV: Rous sarcoma virus promoter; α-gb IVS: mRNA splice donor/splice acceptor of human alpha globin; human FVIIIΔB SQ: human Factor VIII gene; ATG (Kozak): optimized initiation site; syn pA: synthetic poly adenylation site.
Figure 2:
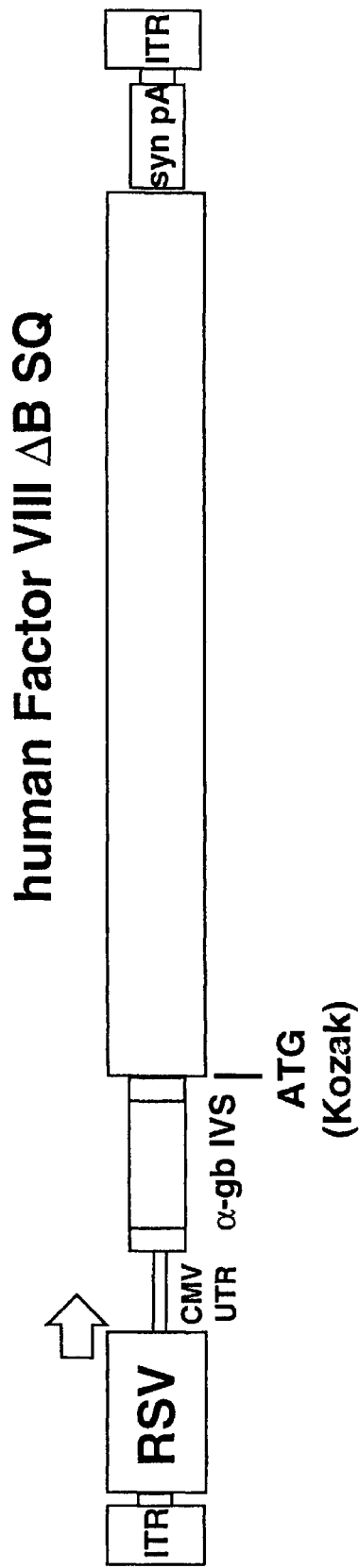
FIG. 2 is a schematic representation of the rAAV-RSV-U-human-Factor VIII vector. ITR: AAV inverted terminal repeat; RSV: *Rous sarcoma* virus promoter; CMV UTR: untranslated region from cytomegalovirus; α-gb IVS: mRNA splice donor/splice acceptor from human alpha globin; human FVIIIΔB SQ: human Factor VIII gene; ATG (Kozak): optimized initiation site; syn pA: synthetic poly adenylation site.
Figure 3:
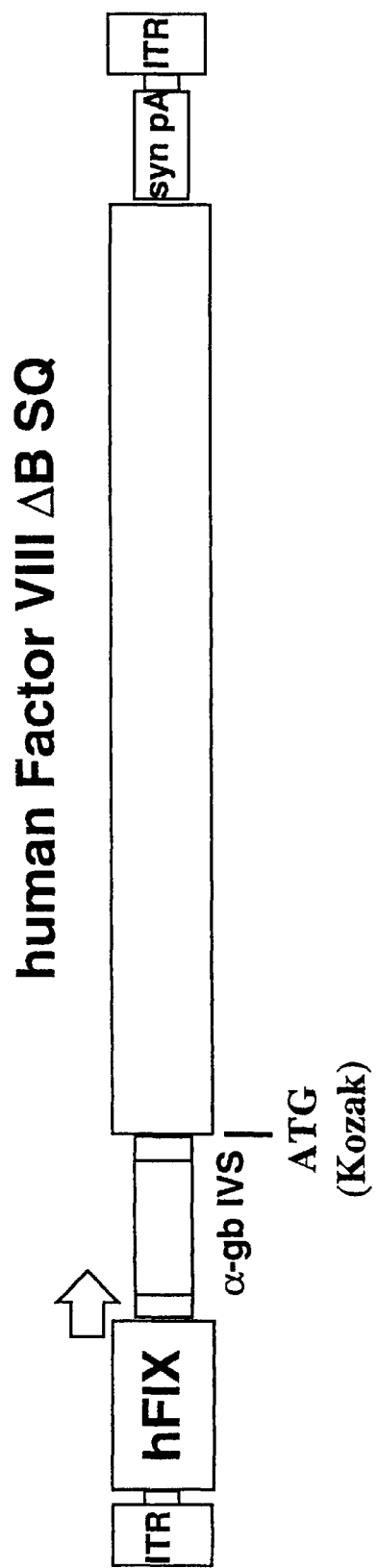
FIG. 3 is a schematic representation of the rAAV-FIX-human-Factor VIII vector. ITR: AAV inverted terminal repeat; hFIX: human factor IX promoter; α-gb IVS: mRNA splice donor/splice acceptor from human alpha globin; human FVIIIΔB SQ: human Factor VIII gene; ATG (Kozak): optimized initiation site; syn pA: synthetic poly adenylation site.
Figure 4:
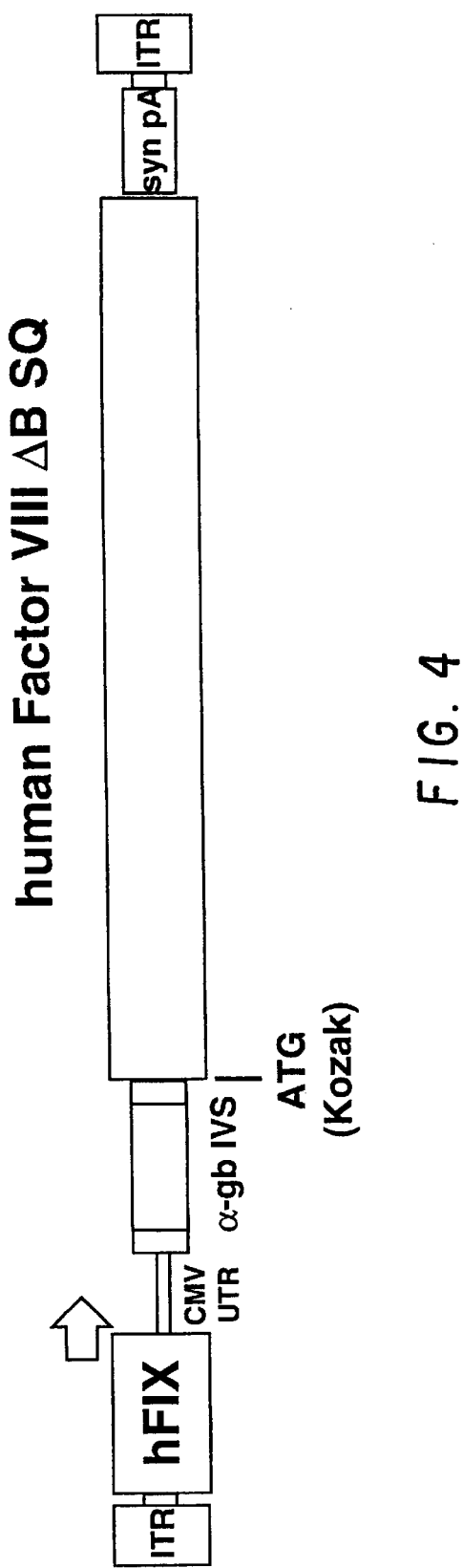
FIG. 4 is a schematic representation of the rAAV-FIX-U-human-Factor VIII vector. ITR: AAV inverted terminal repeat; hFIX: human factor IX promoter; CMV UTR: untranslated region from cytomegalovirus; α-gb IVS: mRNA splice donor/splice acceptor from human alpha globin; human FVIIIΔB SQ: human Factor VIII gene; ATG (Kozak): optimized initiation site; syn pA: synthetic poly adenylation site.
Figure 5:
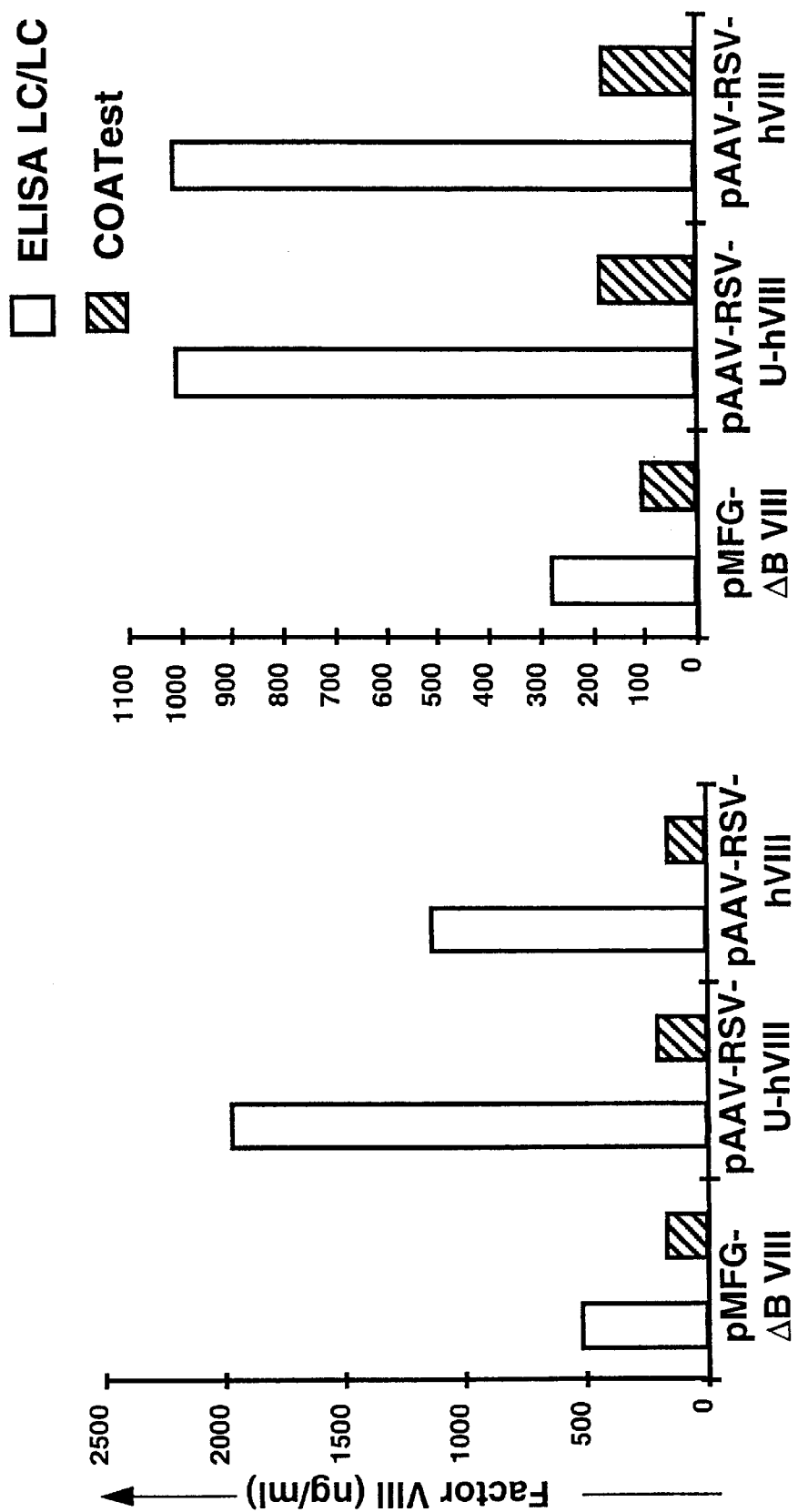
FIG. 5 is a graph showing that functional factor VIII is made following transfection of 293 cells with pMFGΔBVIII (Dwarki et al., PNAS, 92:1023–1027 (1995)), pAAV-RSV-U-hVIII and pAAV-RSV-hVIII vectors. Two separate experiments are shown where Factor VIII activity was measured by COATest and the presence of Factor VIII protein was detected using an ELISA assay to the light chain (LC).
Figure 6:
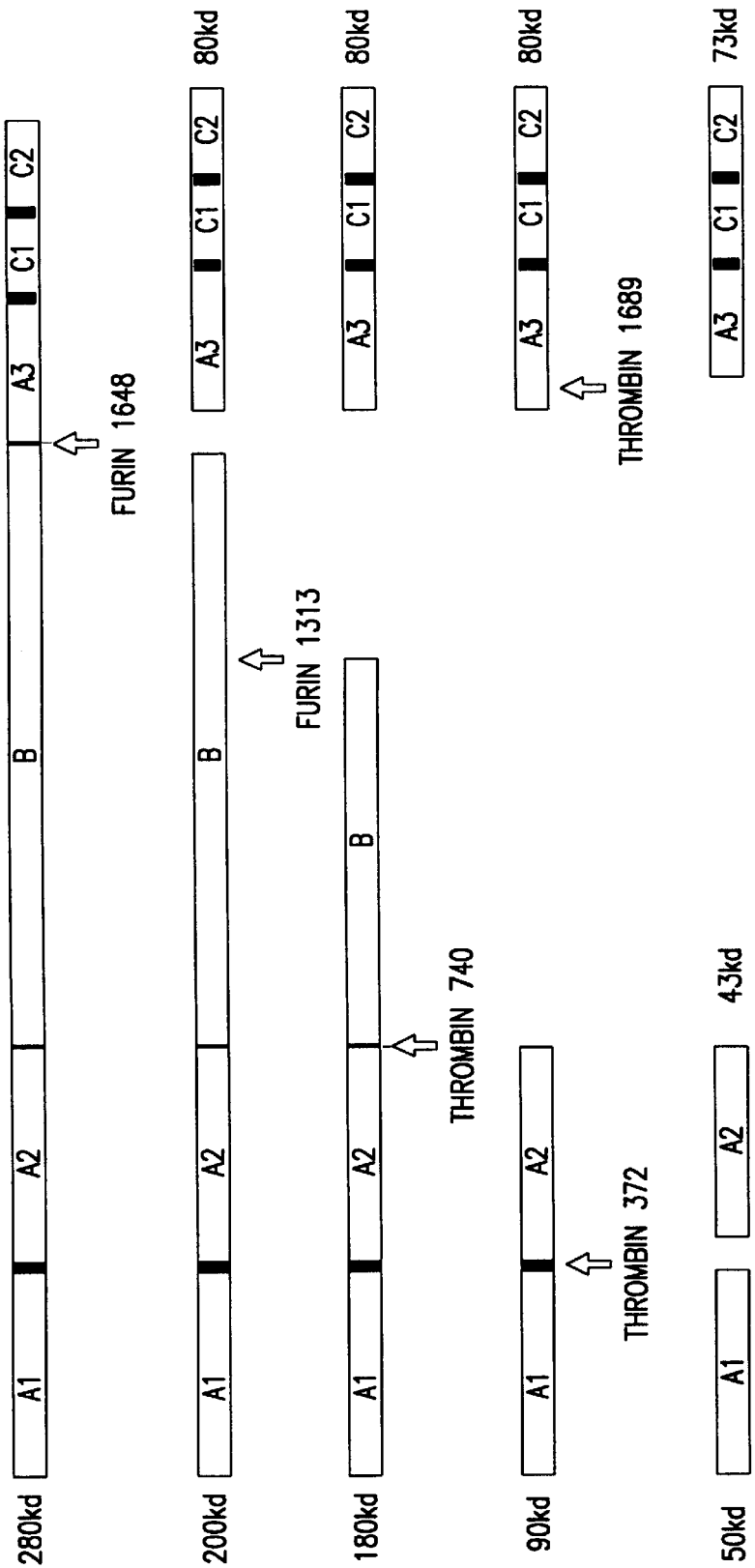
FIG. 6 is a schematic representation of the proteolytic processing of Factor VIII to produce the active protein.
Figure 7:
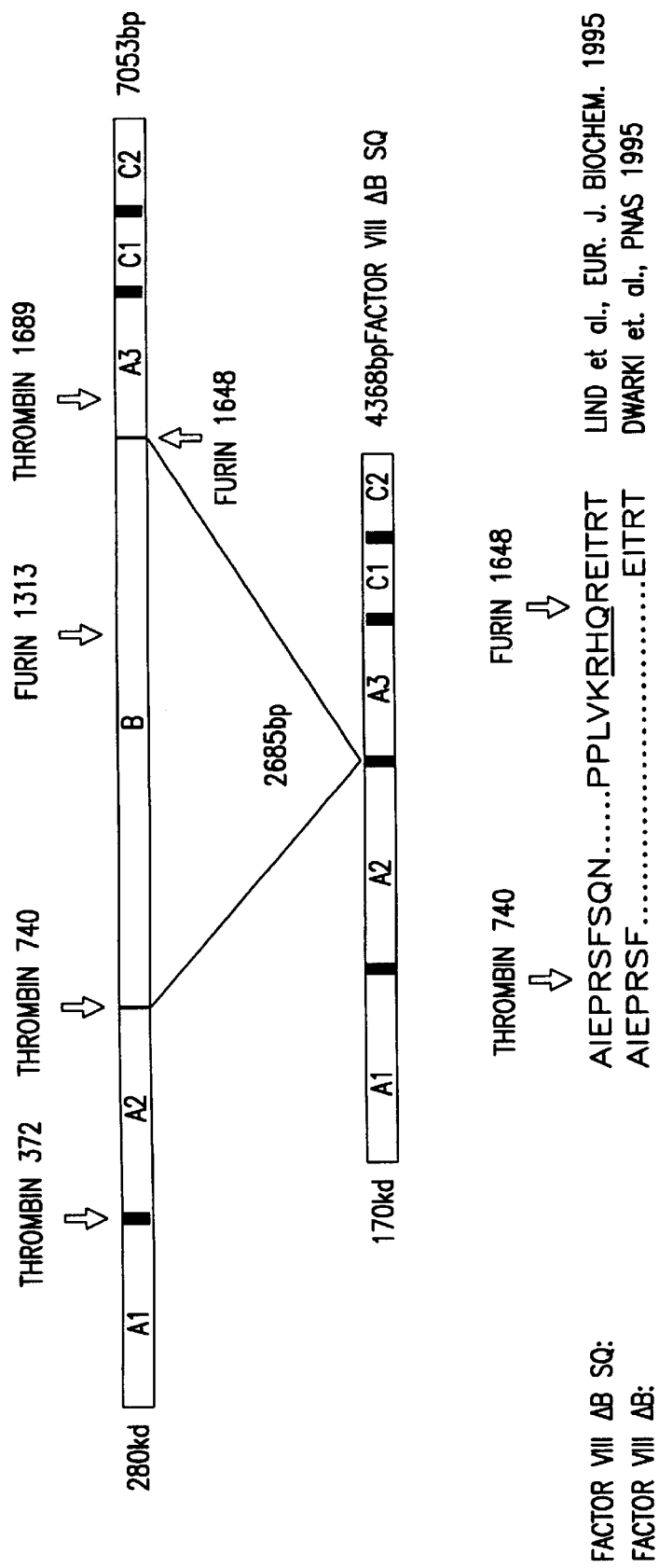
FIG. 7 is a schematic representation of the SQ B domain deletion (Lind et al., Eur. J. Biochem., 232:19–27 (1995) and EP 0 786 474).
Figure 8:
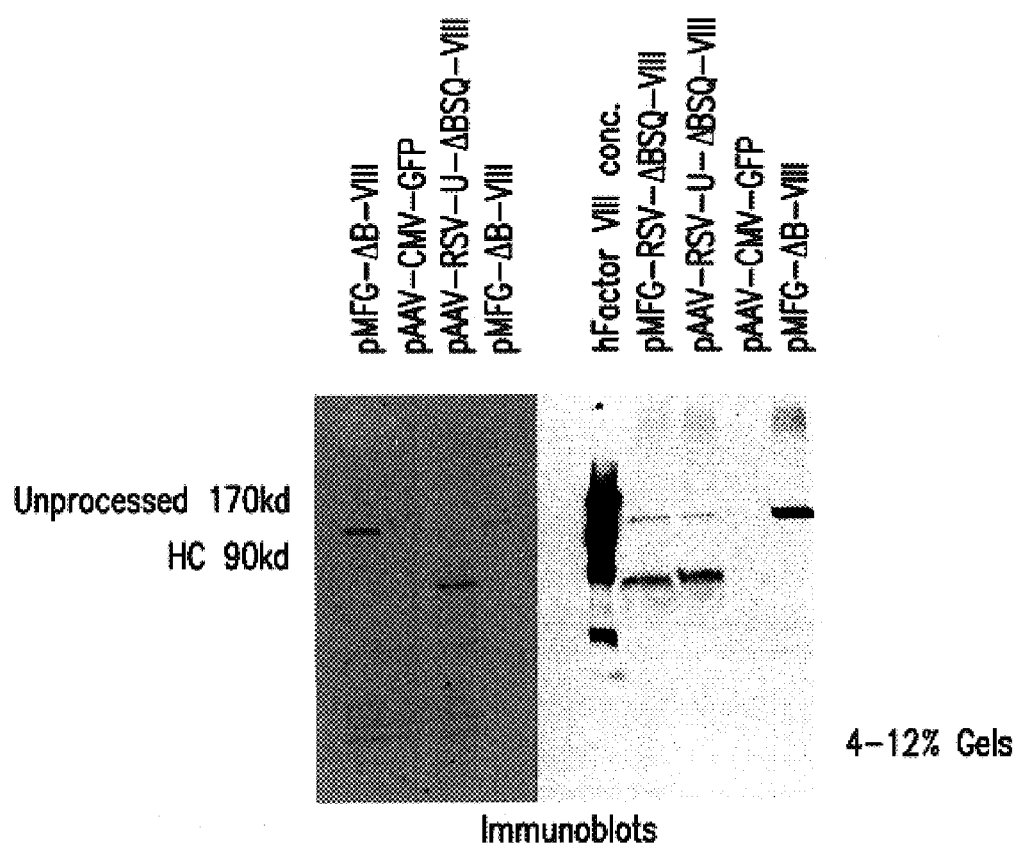
FIG. 8 is a computer generated representation of an analysis to show that the factor VIII protein is properly proteolytically cleaved following transfection of 293 cells with pMFGΔBVIII (Dwarki et al., PNAS, 92:1023–1027), pAAV-RSV-U-hVIII and pAAV-RSV-hVIII vectors. Two separate experiments are shown. The presence of Factor VIII protein is detected by immunoblotting with an anti-factor VIII antibody. The migration of the unprocessed 170 kd and processed 90 kd heavy chain (HC) of FVIII are indicated. pAAV-CMV-GFP is a plasmid vector expressing the green fluorescent protein described by Zolotukhin et al. (J. Virol., 70:4646–4654) which served as a negative control. hFactor VIII conc. is a positive control.
Figure 9:
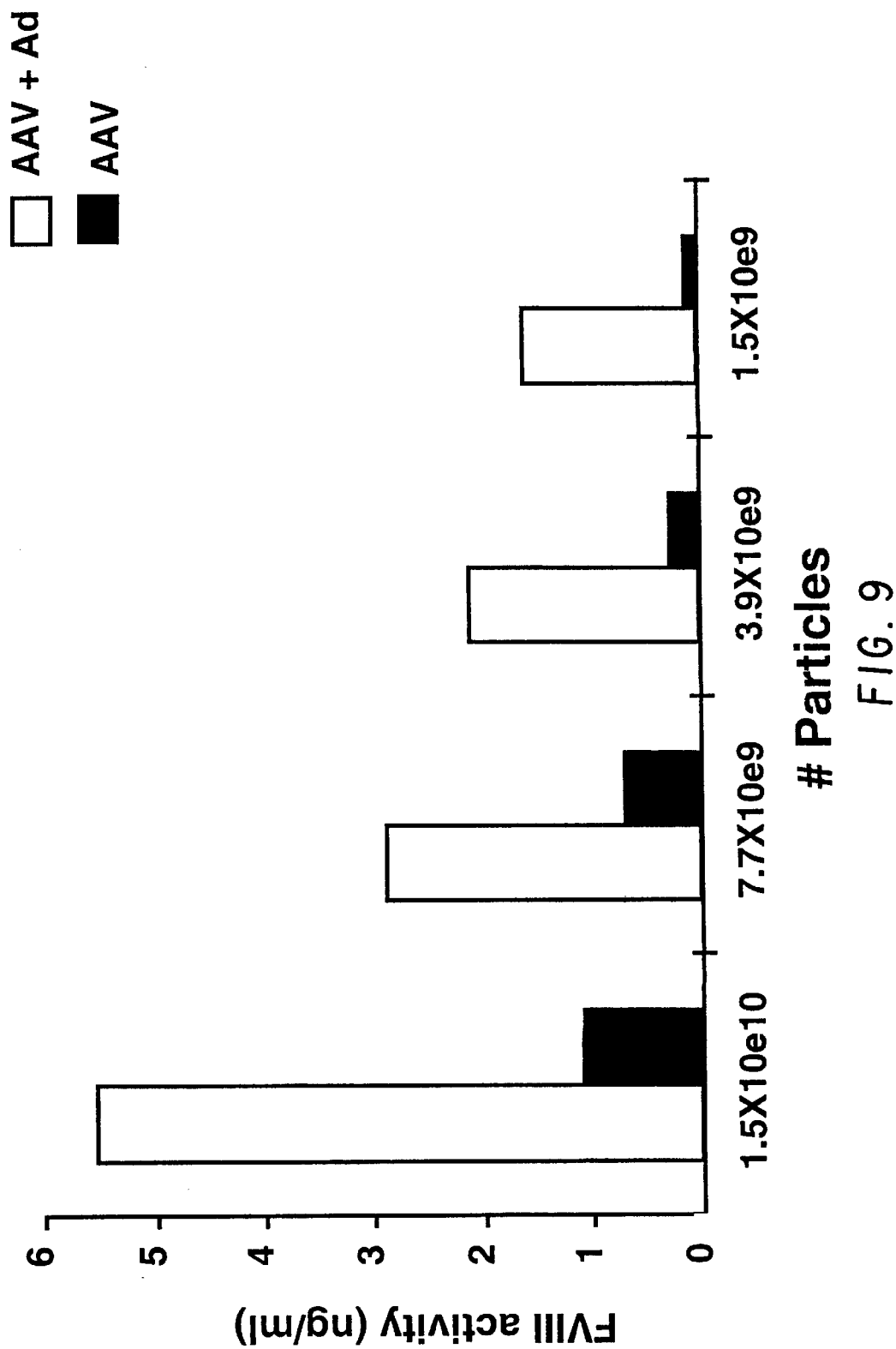
FIG. 9 is a graph showing that functional factor VIII is made following infection of 293 cells in the presence or absence of adenovirus with the indicated number of particles of rAAV-RSV-hFVIII virus. Factor VIII activity was measured by COATest.
Figure 10:
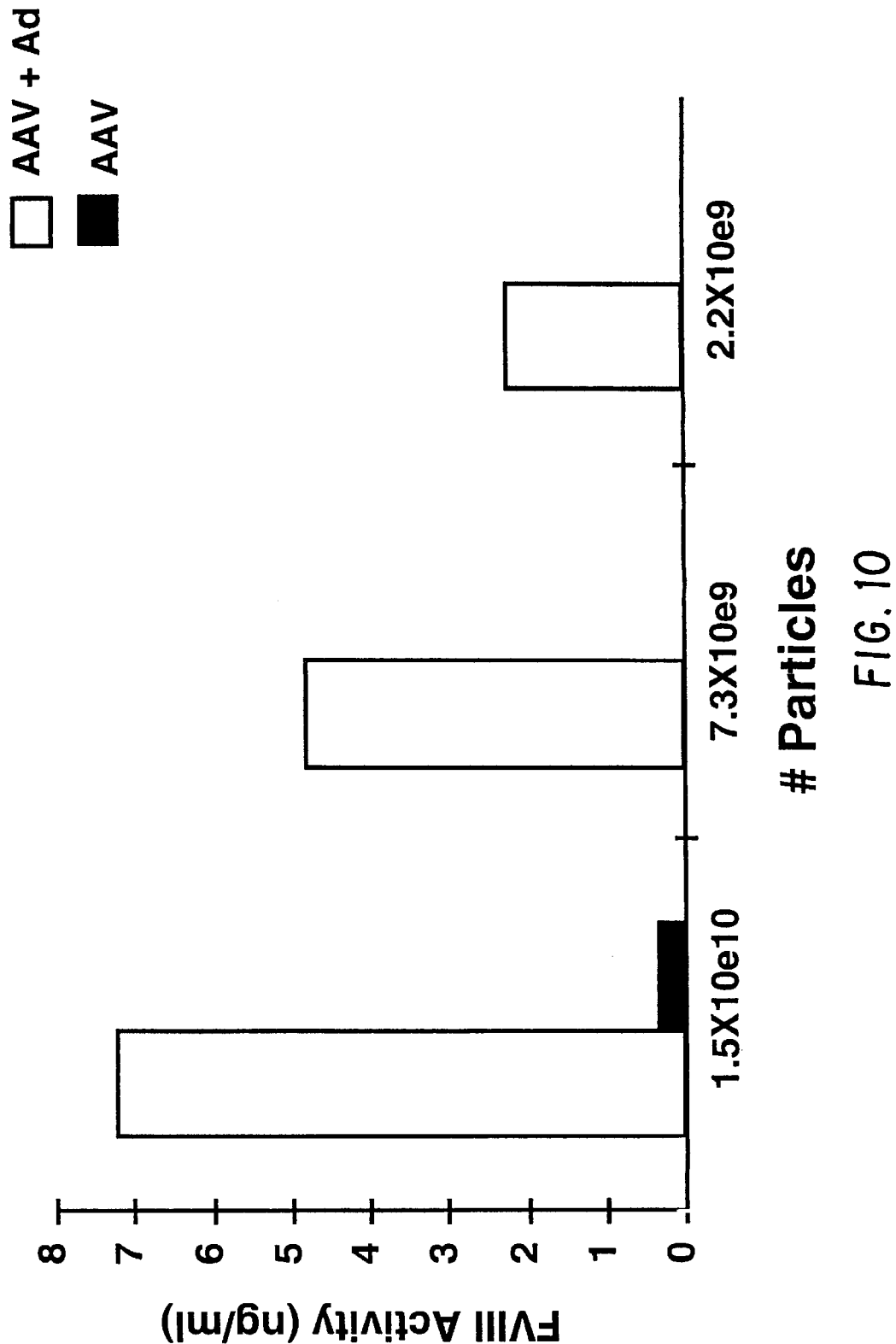
FIG. 10 is a graph showing that functional factor VIII is made following infection of 293 cells in the presence or absence of adenovirus with the indicated number of particles of rAAV-RSV-U-hFVIII virus. Factor VIII activity was measured by COATest.
Figure 11:
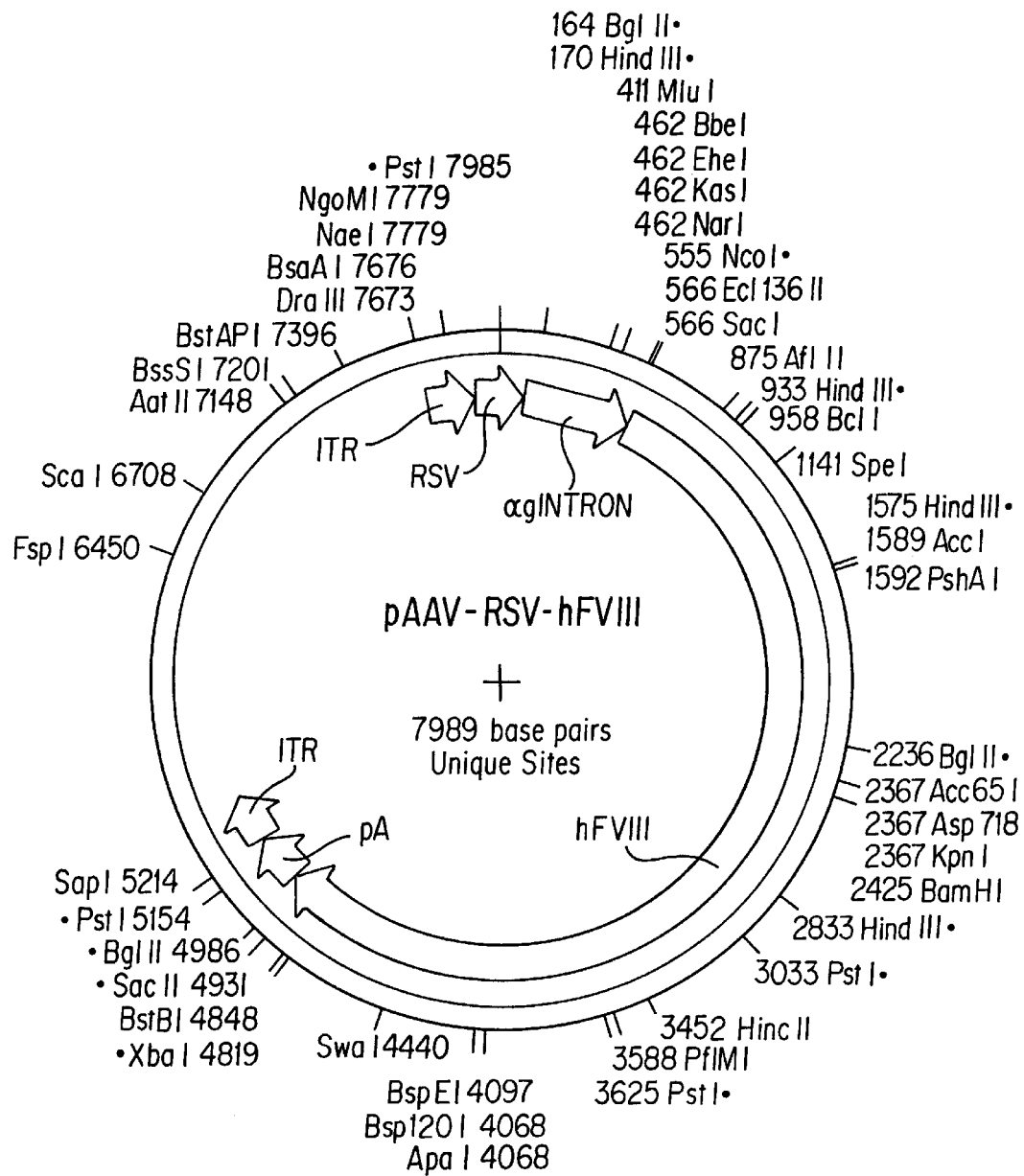
FIG. 11 is a diagram of the pAAV-RSV-hFVIII vector.
Figure 12:
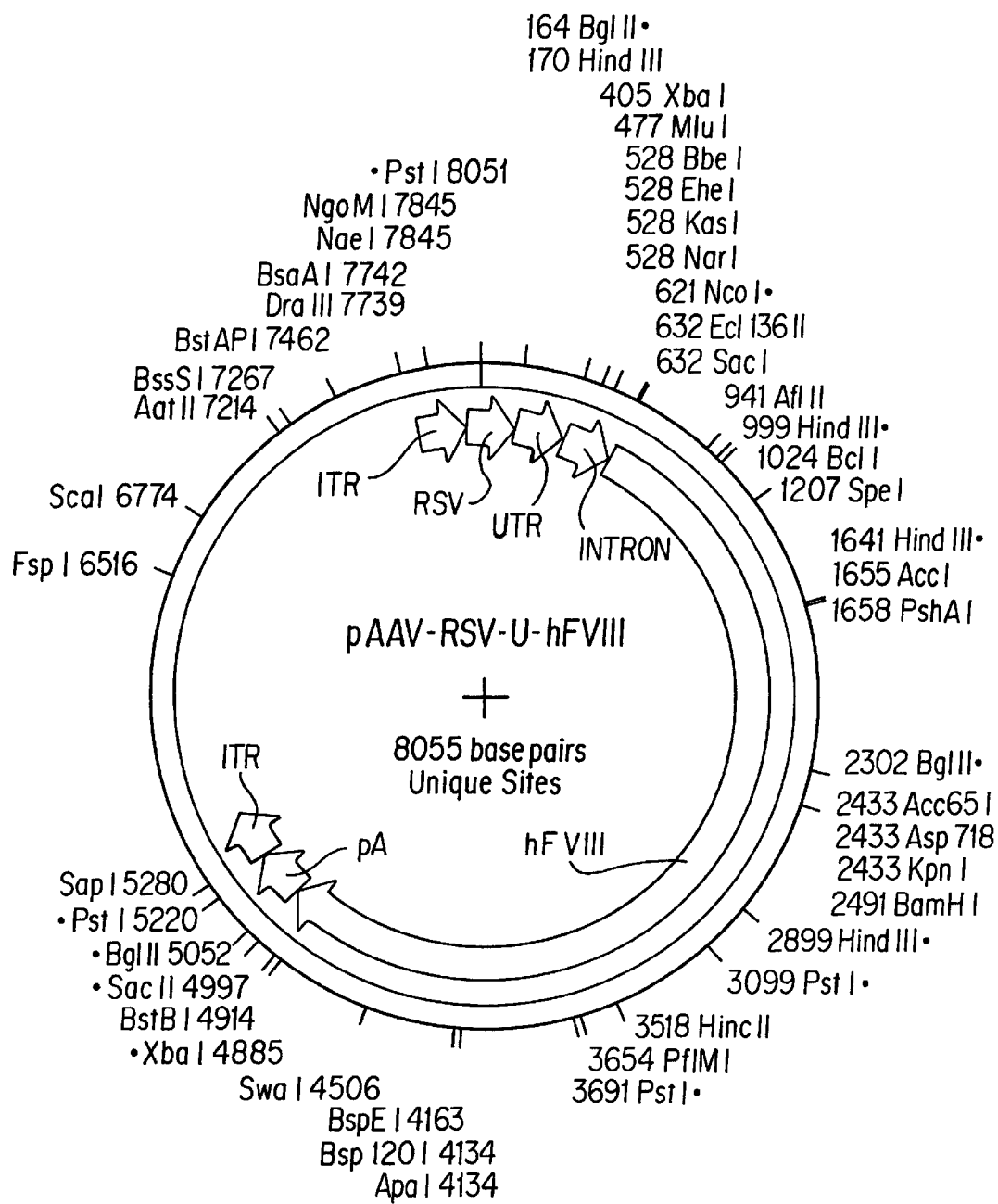
FIG. 12 is a diagram of the pAAV-RSV-U-hFVIII vector.
Figure 13:
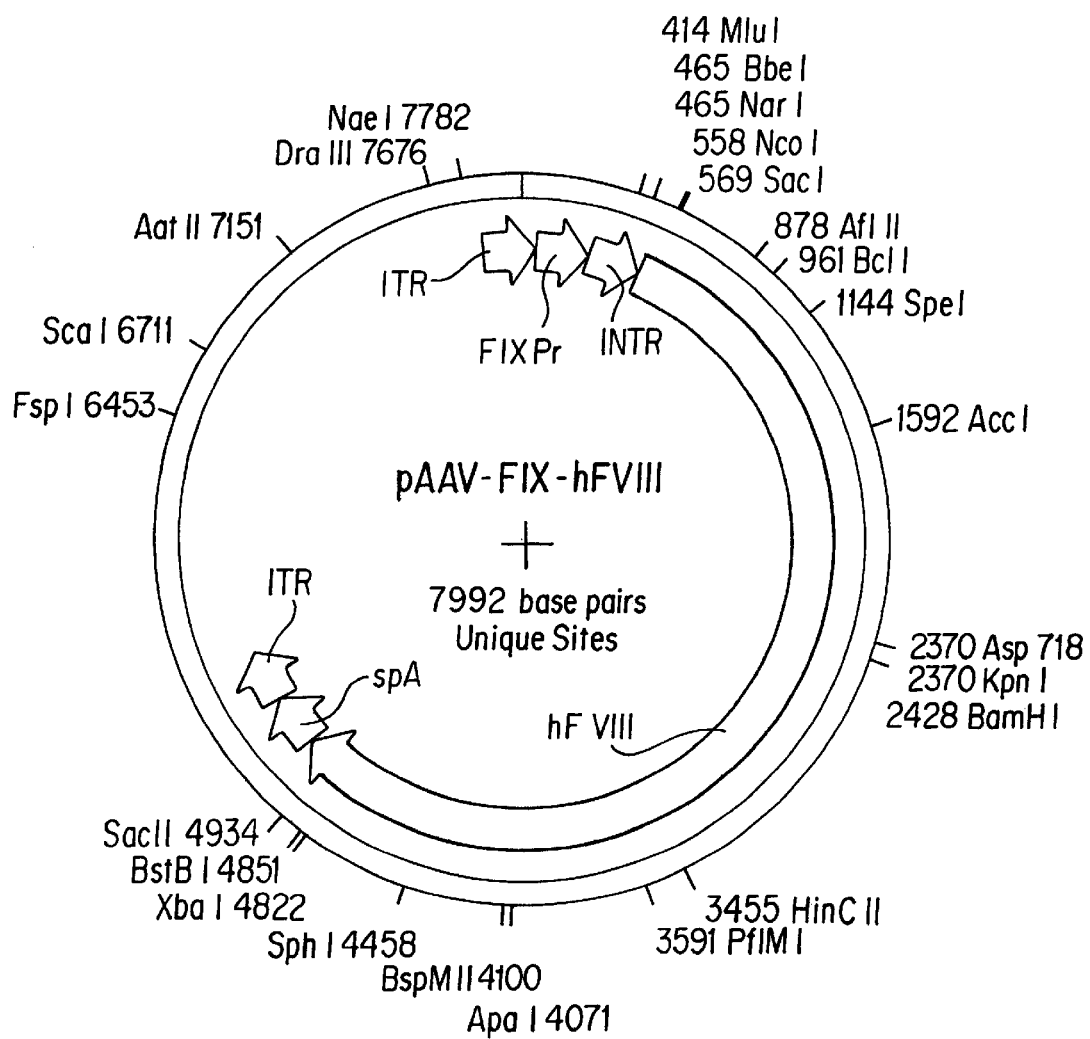
FIG. 13 is a diagram of the pAAV-FIX-hFVIII vector.
Figure 14:
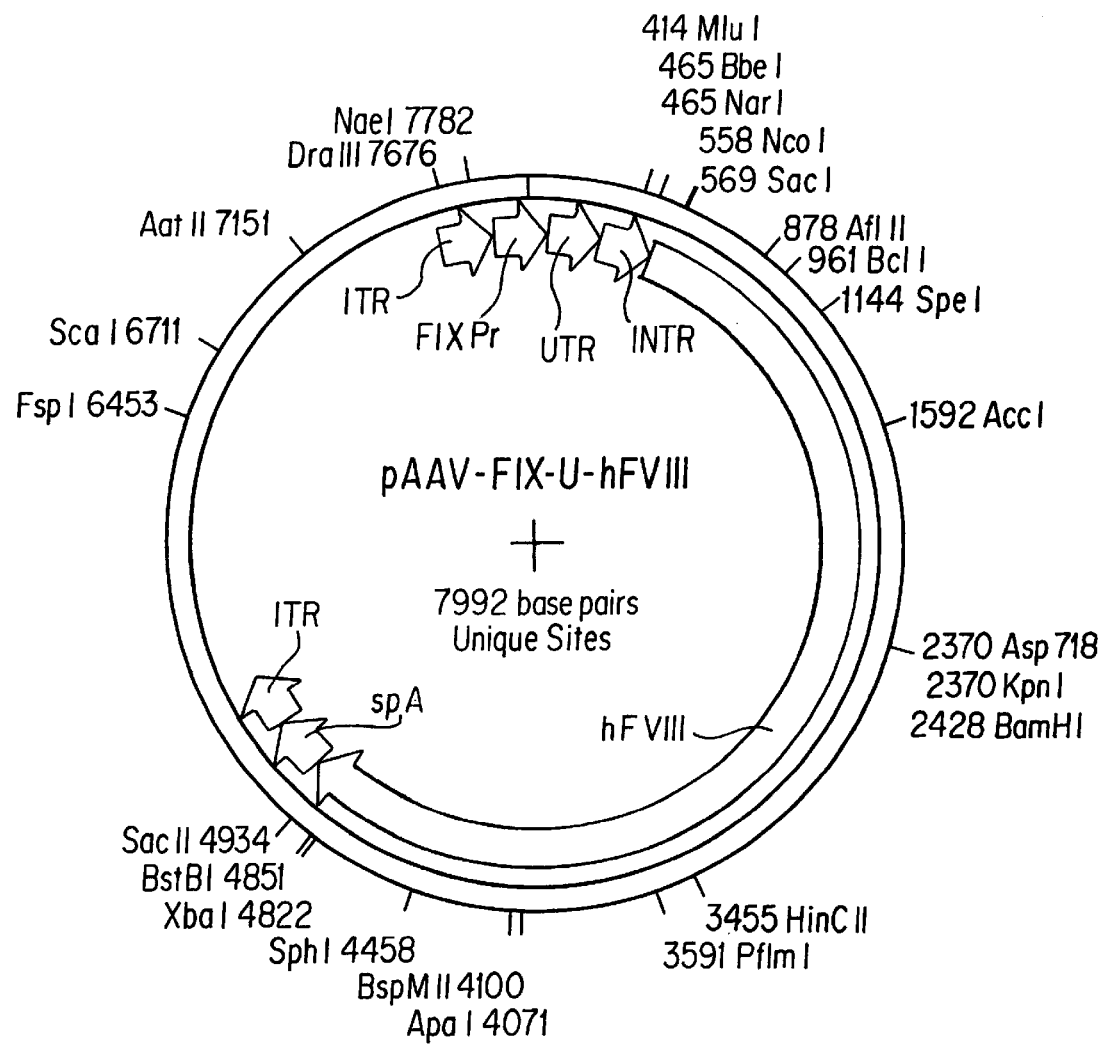
FIG. 14 is a diagram of the pAAV-FIX-U-hFVIII vector.

The rAAV vectors of the instant invention are derivatives of the adeno-associated virus, into which Factor VIII sequences have been introduced, of which various sequences have been modified.

While the wild-type adeno-associated virus is defective in requiring helper virus for lytic infection, there is the possibility that the subject to whom the vector is delivered will harbor a herpesvirus or adenovirus infection which can complement the rAAV vectors and lead to production of rAAV vectors. To guard against that possibility, the rAAV vectors are modified to reduce the possibility of rescue. In theory, such modifications can take the form of point mutations of one or more viral genes, which mutations either prevent expression of the gene altogether or result in the expression of a modified gene product which is nonfunctional. However, point mutations can be reversible. Consequently, it is preferable that each undesired adeno-associated virus gene simply be deleted, which has the additional advantage of creating more room within the viral package for larger foreign nucleic acids such as the Factor VIII gene and associated regulatory elements.

It is preferable that all of the viral genes be deleted from the rAAV vectors, or otherwise inactivated, as in the known AAV vector dl3–94, see, e.g., McLaughlin, J. Virol., 62:1963–1973 (1988). However, it should be understood that an rAAV vector retaining one or more AAV genes, such as the known AAV vector, dl52–91, still may be useful for gene delivery, although possibly inferior to a preferred vector containing no functional AAV genes; see Hermonat, J. Virol., 51:329–339 (1984). Preferably, the rAAV vectors retain from AAV essentially only the recognition signals for replication and packaging (ITR).

The precise nature of regulatory regions needed for gene expression may vary from organism to organism, but in general, include a promoter which directs the initiation of RNA transcription in the cell of interest. Such regions may include those 5'-non-coding sequences involved with initiation of transcription, such as the TATA box. The promoter may be constitutive or regulated. Constitutive promoters are those which cause an operably linked gene to be expressed essentially at all times. Regulated promoters are those which can be activated or deactivated. Regulated promoters include inducible promoters, which are usually "off" but which may be induced to turn "on", and "repressible" promoters, which are usually "on" but may be turned "off". Many different regulators are known, including temperature, hormones, cytokines, heavy metals and regulatory proteins. The distinctions are not absolute; a constitutive promoter may be regulated to some degree.

The regulation of a promoter may be associated with a particular genetic element, often called an "operator", to which an inducer or repressor binds. The operator may be modified to alter the regulation thereof. Hybrid promoters may be constructed in which the operator of one promoter is transferred into another.

The promoter may be a "ubiquitous" promoter active in essentially all cells of the host organism (e.g. the beta-actin or cytomegalovirus promoters) or may be a promoter with expression more or less specific to the target cells (albumin promoter). Preferably, the tissue-specific promoters are essentially not active outside, for example, the hepatic system, and the activity of the promoter optionally may be higher in some components of the hepatic system than in others.

Thus, the promoter may be one which is active primarily in the hepatic system. The specificity may be absolute or relative. Similarly, the promoter may be specific for particular cell types, including but not limited to hepatocytes, Kupffer cells or endothelial cells.

In general, to locate a tissue-specific promoter, one identifies a gene which is expressed only (or primarily) in that tissue and then isolates the gene encoding that protein. (The gene may be a normal cellular gene, or a viral gene of a virus which infects that cell.) The promoter of that gene is likely to retain the desired tissue-specific activity when linked to another gene. The tissue specificity of a promoter may be associated with a particular genetic element, which may be modified or transferred into a second promoter.

One of ordinary skill in the art will appreciate that a tissue-specific promoter for use in an AAV vector may be selected from any of the known liver-specific promoters and enhancers, including the albumin promoter; the alphafetoprotein promoter (Genbank Accession No. L34019); alphafetoprotein enhancer; human apolipoprotein E (ApoE) gene promoter and its associated liver-specific enhancers HCR-1 and HCR-2 (Nguyen et al., Oncogene, 12(10): 2109–2119 (1996) and Allen et al., J. Biol. Chem., 270(44): 26278–26281 (1995)); the factor VIII promoter (GenBank No. M14113); the factor IX promoter (Salier et al., (1990), infra); the vWF promoter (Gnatenko et al., Blood, 90 Suppl., Part 1 of 2:119a (1997); the liver-specific enhancer of apolipoprotein AI (Malik et al., Mol. Cell. Biol., 16(4): 1824–1831 (1996)) and the liver-specific human α1-antitrypsin promoter (Wu et al., Hum. Gene Therapy, 7(2):159–171 (1996) and Hafenrichter et al., Blood, 84(10) :3394–3404 (1994)).

There also are other known strong promoters which find common use to obtain high levels of recombinant protein expression. For example, the herpes simplex thymidine kinase promoter, SV40 promoter and LTR's have found wide use as strong promoters. An example is the LTR obtained from Moloney leukemia retrovirus.

A key feature is the size of the promoter. Because of the size of the factor VIII coding sequence, the sizes of the regulatory elements must be considered in view of the size limitation of AAV for encapsidation to occur.

Suitable promoters for expression of a protein with factor VIII activity in cells of hepatic origin are the Rous sarcoma virus promoter and the human factor IX promoter. Generally, the promoter must be no longer than about 800 bp. A consideration is the size as well as the activity of the promoter. Generally, a smaller sized promoter is preferable. Thus, some of the promoters used herein are about 250 bp in size. An artisan can optimize the size and activity of a promoter practicing methods as taught herein.

For the gene to be expressed, the coding sequence must be operably linked to a promoter sequence functional in the target cell. A promoter region would be linked operably to a coding sequence if the promoter were positioned so that, when the promoter was activated, the coding sequence was transcribed. The coding sequences are linked operably if the linkage does not cause an error in the reading of the downstream sequence. To be "operably linked" it is not necessary that two sequences be immediately adjacent to one another.

The rAAV vectors may further comprise one or more restriction sites into which polynucleotides carrying an FVIII domain or domains may be cloned without interfering with packaging and replication. Preferably, at least one unique restriction site is provided.

As to optional mRNA slice donor/splice acceptor sequences, associated with intervening sequences, any such donor/acceptor sequences compatible with and operable in AAV can be used. Particular, non-limiting examples of suitable donor/acceptable sites are taught herein and are known in the art. For example, the α-globin intervening sequence is provided in some of the examples hereinbelow. McCullough & Berget, Mol. Cell. Biol., 17:4562–4571, teach another example of a suitable intervening sequence. As discussed hereinabove, the artisan can use other such sequences so long as the desired expression levels are obtained and the overall size of the insert in the AAV is compatible with encapsidation.

As to polyadenylation sites, any such polyadenylation site compatible with and operable in AAV can be used. Particular, non-limiting examples of suitable polyadenylation sites are taught herein and all known in the art. For example, the poly-A sequence of Levitt et al., infra, can be used as well as synthetic derivatives thereof. Goodwin (JBC, 267:16330–16334 (1992)), Bohnlein (J. Virol., 63:421–424 (1989)) and Fitzgerald & Shenk (Cell, 24:251–260 (1981)) teach other suitable poly-A sites and synthetic derivatives thereof. The artisan can use any poly-A site so long as expression is optimized and the size thereof is such that encapsidation is not impeded.

If desired, the non-coding region 3' to the gene sequence coding for the desired RNA product may be obtained. The region may be retained for its transcriptional termination regulatory sequences, such as those which provide for termination and polyadenylation. Thus, by retaining the 3' region naturally contiguous to the coding sequence, the transcriptional termination signals may be provided. Where the transcriptional termination signals natively associated with the coding sequence are not satisfactorily functional in the expression host cell, then a different 3' region, functional in the host cell, may be substituted.

Kozak, (1987), infra, teaches optimized initiation sites and the artisan can modify the sequences flanking the ATG to obtain optimized expression of the polypeptide with FVIII activity. Generally, the changes are substitutions but insertions can be tolerated if there is not a substantial increase in size of the polynucleotide framed by the ITR's. Kozak (J. Cell. Biol., 108:229–241 (1989)) also teaches alterations which enhance initiation.

Also, the vector of interest can include a spacer identified as an untranslated region (UTR) which is situated between the 3' and of the promoter and the initiation codon of the factor VIII polypeptide. Again, the size of the untranslated region must consider the size of the polynucleotide flanked by the ITR's and the optimal activity. A suitable such spacer is the 5' UTR of cytomegalovirus.

As to the AAV inverted terminal repeats, any such ITR's or derivatives thereof, which contain nucleotide substitutions, deletions, inversions and/or insertions yet retain the requisite biological activities required of an AAV vector carrying a foreign gene, can be used. Also, ITR's from different AAV serotypes can be used.

Another element which contributes to the proper expression of FVIII is a signal sequence. A suitable signal sequence is that of native FVIII.

It is not necessary that the AAV-derived sequences correspond exactly with wild-type AAV prototypes. For example, the rAAV vectors of the instant invention may feature modified inverted terminal repeats and other sequences, provided that the rAAV vectors can replicate and be packaged with the assistance of helper virus, and establish a nonpathogenic latent infection in target cells.

Typically, because of the packaging limitations of AAV, the polynucleotides encoding FVIII domain sequences and the regulatory elements can have a length of up to about 5,500 bases.

The AAV-derived helper virus or helper plasmid may be any virus or plasmid which is capable, on expression of the AAV genes it carries, of providing proteins necessary for the replication and packaging of the rAAV vector in a suitable host cell, for the purpose of producing rAAV vector stock.

Moreover, in a preferred embodiment, the helper virus or helper plasmid is one which has been engineered to reduce the risk of recombination between the AAV helper DNA and the rAAV vector DNA. More desirably, there is very limited or no sequence homology between the AAV sequences of the vector DNA and the AAV sequences of the helper DNA. For example, the helper DNA may be an AAV sequence in which the AAV inverted terminal repeats are replaced by the corresponding sequences of another virus, such as adenovirus (e.g., adenovirus type 5 DNA), see Samulski et al. (1989), supra.

As to the non-AAV helper virus, generally that is one in which a gene necessary for replication is made defective. For example, an adenovirus stock wherein a gene thereof, such as the E1A gene, is disabled.

Non-AAV helper virus may be removed by heat inactivation at about 56° C. for about 30–45 minutes, or physically separated from packaged rAAV vectors by any of a variety of methods, including single or multiple centrifugation runs in a cesium chloride gradient.

For propagation of the rAAV vectors in vitro, susceptible cells are co-transfected with an AAV-derived vector DNA and a suitable AAV-derived helper virus or plasmid harboring the AAV rep gene, AAV cap gene or both and infected by a helper virus, including herpesvirus, adenovirus or a suitable non-AAV helper plasmid. The particular method of producing viral particles is not critical to the invention. Any method of producing the rAAV viral particles can be used, including but not limited to that described in Samulski et al. (1989), supra, so long as appropriate concentrations of viral particles capable of transducing cells in vivo and ex vivo are obtained. One of ordinary skill in the art will appreciate that any purification method used should produce infectious viral particles able to transduce hepatic cells in vivo or ex vivo.

Because of the size constraints for forming an AAV particle, the sequence encoding a polypeptide with factor VIII activity is one where most sequences not needed for factor VIII activity are removed. Thus, at least the 90 kD heavy chain and the light chain, without the B domain, are present in a vector of interest. Various further modifications thereto, such as removal of additional sequences can be tolerated so long as the desired levels of factor VIII activity and of encapsidation efficiency are not compromised.

Basic procedures for constructing recombinant DNA and RNA molecules in accordance with the instant invention are disclosed in numerous publications, including Sambrook et al., In: Molecular Cloning: A Laboratory Manual, Second Edition, Cold Spring Harbor Press, Cold Spring Harbor, N.Y. (1989), which is herein incorporated by reference.

The instant invention may be used for gene therapy of Factor VIII associated disorders, such as hemophilia A. An individual may be in need of gene therapy because, as a result of one or more mutations in the regulatory region and/or the coding sequence of the Factor VIII gene, Factor VIII is expressed inappropriately, e.g., has an incorrect amino acid sequence, or is expressed in the wrong tissues or at the wrong times, is underexpressed or overexpressed.

The target cells of the vectors of the instant invention are cells capable of expressing polypeptides with FVIII activity, such as those of the hepatic system of a mammal, endothelial cells and other cells with the proper machinery to process the precursor to yield protein with factor VIII activity. In one embodiment, the cells are normal cells cultured in vitro. The target cells may be human cells, or cells of other mammals, especially nonhuman primates and mammals of the orders Rodenta (mice, rats, rabbit and hamsters), Carnivora (cats and dogs) and Arteriodactyla (cows, pigs, sheep, goats and horses).

In another embodiment, the cells are part of a living mammal at the time the rAAV vectors are delivered to the cell. The mammal may be at any stage of development at the time of delivery, e.g., embryonic, fetal, infantile, juvenile or adult. Additionally, the cells may be healthy or diseased.

To deliver the vectors specifically to a particular region of, for example, the liver, they may be administered by intraportal injection. Because the AAV vectors will be maintained stably in the target cells, rather than producing viral particles, the subsequent spread of the vector will be minor and will be mainly a function of passive diffusion from the site of injection. The degree of diffusion may be controlled by adjusting the ratio of rAAV vectors to fluid carrier.

In certain embodiments, the vectors will be administered via an intravascular approach. For example, the vectors can be administered intra-arterially. Of course, with intravenous as well as intraportal delivery, the recipient mammal must be able to tolerate the possibility of delivery of the vectors to cells other than those of the hepatic system.

For targeting the vectors to a particular type of cell, e.g., hepatocytes, it may be beneficial to associate the vector with a homing agent that binds specifically to a surface receptor of the cell. Thus, the vectors may be conjugated to a ligand (e.g., galactose) for which certain hepatic system cells have receptors. The conjugation may be covalent, e.g., a crosslinking agent such as cross-linking agents (e.g. glutaraldehyde), or noncovalent, e.g., the binding of an avidinated ligand to a biotinylated vector. Another form of covalent conjugation is provided by engineering the AAV helper plasmid used to prepare the vector stock so that one or more of the encoded coat proteins is a hybrid of a native AAV coat protein and a peptide or protein ligand, such that the ligand is exposed on the surface of the viral particle.

Whatever the form of conjugation, it must not interfere substantially either with the production or transduction of the rAAV vectors.

The rAAV vectors may be administered as viral particles alone, whether as an in vivo direct delivery to the portal vasculature or as an ex vivo treatment comprising administering the rAAV vector viral particles in vitro to cells from the animal receiving treatment followed by introduction of the transduced cells back into the donor. Alternatively, the rAAV vector virus particles can be used to transduce cells in conjunction with secondary agents known to enhance the efficiency of transduction, see, e.g., WO Ser. No. 95/33824 for a variety of secondary agents. Secondary agents useful for enhancing transduction efficiency include radioactive molecules, including tritiated nucleotides, ultraviolet radiation, gamma irradiation, cis-platinum, hydroxyurea, etoposide, camptothecin, aphidicolin and adenovirus, see e.g., Ferrari et al., J. Virol., 70:3227–3234 (1996).

Prior to administration to a host, it is beneficial to determine the purity of the recombinant AAV preparation, that is, the AAV vector containing the transgene. For example, while no diseases are associated with AAV infection, knowing the degree of wild-type AAV contamination in a recombinant virus preparation is desirable. Wild-type virus can be generated by cross over between, for example, the AAV helper plasmid and the AAV plasmid carrying the transgene.

The presence of contaminating wild-type AAV can be determined, for example, by a nucleic acid amplification assay, such as PCR or an RNA based amplification method such as 3SR (Gingeras et al., Ann. Biol. Clin., 48:498–501 (1990)) and NASBA (van der Vleit et al., J. Gen. Micro., 139:2423–2429 (1993)).

Thus, in the case of PCR, AAV nucleic acid is prepared and subjected to a PCR reaction, along with positive and negative controls. The strategic identification of certain PCR primers enables distinguishing wild-type from recombinant virus in an expeditious and efficient fashion. Thus, primers are selected to be specific for wild-type AAV or for wild-type AAV derived through recombination of the helper and vector plasmids.

AAV vectors derived from pSub201 (Samulski et al., J. Virol., 61:3096–3101 (1987)) or other vectors tailored to have distinctive sequences in the left and right arms of the vector enable distinguishing wild-type virus from wild-type virus arising from recombination. By left and right arms, it is meant to refer to those portions of the vector which flank the cloning site which contains the transgene. Thus, in the case of pSub201, the left arm is that portion to the left of the XbaI site and the right arm is that portion to the right of the XbaI site. The arms contain the hairpin structures.

Referring to the exemplified pSub201 vector to explain the method, it is noted that the pSub201 has sequences found normally on the right arm of AAV are on both sides of the transgene. Thus, sequences found normally only on the right arm are present on the left arm as well, the left sequences having been deleted.

Accordingly, primers can be configured wherein the presence or absence of left sequences or the presence of right sequences on both sides of the virus can be used to distinguish wild-type AAV containing the normally occurring left sequences from any wild-type AAV generated by recombination between the helper and vector plasmids containing right sequences on both sides of the transgene.

For example, when using a pSub201 vector, or equivalent vector containing right arm sequences on both arms, the primers which hybridize to sequences in the AAV ITR in the AAV rep gene; in the AAV splice region; and in the AAV cap gene can be diagnostic.

As to the primers, it will be well appreciated that once suitable sites are located in the two genomes which are found to be diagnostic of wild-type and cross over generated wild-type virus, the exact nucleotide sequence and length of any one primer can be varied without detracting from the object of the diagnostic assay. The limitations to the variations to the primers depend on, for example, the reaction conditions of PCR to assure hybridization of the primer to target.

In the case of NASBA or 3SR, essentially the same primers can be used which will be configured to contain a suitable RNA polymerase promoter. Another primer for synthesis of the double-stranded intermediate can rely on, for example, use of the Cap2 or AAV2S2 primers.

The instant invention includes pharmacological intervention in vivo or ex vivo to treat FVIII-related disorders. The rAAV vectors, which comprise the rAAV vectors (including the ITR's) packaged in viral particles, are administered to a human patient in an amount effective to obtain the desired Factor VIII activity in serum. Administration can be by any means in which the therapeutic polypeptides are delivered to the desired target cells. For example, both in vivo and ex vivo methods are contemplated. Intravenous injection of rAAV vector to the portal vein is a preferred method of administration for transducing liver cells. Other in vivo methods include, for example, direct injection into the lobes of the liver or the biliary duct and intravenous injection distal to the liver. Ex vivo modes of administration include transduction in vitro of resected hepatocytes or other cells of the liver with the rAAV vectors, followed by infusion of the transduced, resected hepatocytes back into the portal vasculature or biliary tree of the human patient, see e.g., Grossman et al., Nature Genetics, 6:335–341 (1994).

Whether the transduction of liver cells occurs in vivo or ex vivo, the rAAV vector virus particles can be delivered either alone or in conjunction with a partial hepatectomy, a helper virus (including, for example, adenovirus, CMV or HSV-1) or a secondary agent for enhancing transduction efficiency.

The effective amount of rAAV vectors to be administered will vary from patient to patient. Accordingly, effective amounts are best determined by the physician administering the rAAV vectors and appropriate dosages can be determined readily by one of ordinary skill in the art. A useful initial amount for administration may be in the range from $10^9$ to $10^{20}$ particles for a 70 kg adult. After allowing sufficient time for the rAAV vectors to be expressed (typically 4–15 days, for example), analysis of the serum or other tissue levels of Factor VIII activity and comparison to the initial level prior to administration will determine whether the amount being administered is too low, within the right range or too high.

Suitable regimes for initial and subsequent administrations also may be variable, but are typified by an initial administration followed by subsequent administrations, if necessary. Subsequent administrations may be administered at variable intervals, ranging from daily to annually to every several years. One of skill in the art will appreciate that appropriate immunosuppressive techniques may be recommended to avoid inhibition or blockage of transduction by immunosuppression of the rAAV viral vectors, see e.g., Vilquin et al., Human Gene Ther., 6:1391–1401 (1995).

Formulations for both ex vivo and in vivo administrations include suspensions in liquid or emulsified liquids. The active ingredient (rAAV vector) often is mixed with excipients which are pharmaceutically acceptable and compatible with the active ingredient. Suitable excipients include, for example, water, saline, dextrose, glycerol, ethanol or the like, and combinations thereof. In addition, the composition may contain minor amounts of auxiliary substances, such as, wetting or emulsifying agents, pH buffering agents, stabilizing agents or other reagents that enhance the effectiveness of the pharmaceutical composition.

Pharmaceutical compositions can be prepared as injectable formulations for administration as known in the art, including the use of implantable pumps (known by those of skill in the art and described, for example, in U.S. Pat. No. 5,474,552). Numerous formulations for oral or parenteral administration are known and can be used in the practice of the instant invention. The vectors can be used with any pharmaceutically acceptable carrier for ease of administration and handling.

For parenteral administration, solutions in an adjuvant such as sesame or peanut oil or in aqueous propylene glycol can be employed, as well as sterile aqueous solutions. Such aqueous solutions can be buffered, if desired, and the liquid diluent first rendered isotonic with saline or glucose. Solutions of the AAV vector as a free acid (DNA contains acidic phosphate groups) or a pharmacologically acceptable salt can be prepared in water suitably mixed with a surfactant such as hydroxypropylcellulose. A dispersion of AAV viral particles also can be prepared in glycerol, liquid polyethylene glycols and mixtures thereof and in oils. Under ordinary conditions of storage and use, the preparations contain a preservative to prevent the growth of microorganisms. The sterile aqueous media employed are obtainable by standard techniques well known to those skilled in the art.

The pharmaceutical forms suitable for parenteral administration include sterile aqueous solutions or dispersions and sterile powders for the extemporaneous preparation of sterile injectable solutions or dispersions. In all cases the form must be sterile and must be fluid to the extent that parenteral administration is possible. The formulation must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, liquid polyethylene glycol and the like), suitable mixtures thereof, and vegetable oils. The proper fluidity can be maintained, for example, by the use of a coating such as lecithin, by the maintenance of the required particle size in the case of a dispersion and by the use of surfactants. The prevention of the action of microorganisms can be brought about by various antibacterial and antifungal agents, for example, parabens, chlorobutanol, phenol, sorbic acid, thimerosal and the like. In many cases it will be preferable to include isotonic agents, for example, sugars or sodium chloride. Prolonged absorption of the injectable compositions can be brought about by use of agents delaying absorption, for example, aluminum monostearate and gelatin.

Sterile parenteral formulations are prepared by incorporating the AAV vector in the required amount in the appropriate solvent with various of the other ingredients enumerated above, as required, followed by filtered sterilization. Generally, dispersions are prepared by incorporating the sterilized active ingredient into a sterile vehicle which contains the basic dispersion medium and the required other ingredients from those enumerated above. In the case of sterile powders for the preparation of sterile injectable solutions, the preferred methods of preparation are vacuum drying and freeze drying which yield a powder of the active ingredient plus any additional desired ingredient from the previously sterile-filtered solution thereof.

The instant recombinant vectors also can be administered orally. Such preparations can be formulated as known in the art and can include, for example, flavorants, odorants, colorings and the like to facilitate presentation.

The invention now being generally described, the same will be better understood by reference to the following examples, which are provided for purposes of illustration only and are not to be considered limiting of the invention.

EXAMPLES

Example 1

Vector Construction pAAV-RSV-hFVIII:

The vector was made by inserting the human factor VIII cDNA sequence into pTRUF5 RSV NSS.3. pTRUF5 RSV NSS.3 was digested with SstI and SstII to yield a 3624 bp isolated fragment. pKS$^+$F8ΔΔNcoTGA was digested with SstI and SstII to yield a 4253 bp isolated fragment. pKS$^+$3'F8 was digested with XbaI and SstII to yield a 126 bp isolated fragment and all 3 pieces were ligated together.

pTRUF5 RSV NSS.3:

The vector was designed to aid the replacement of the human FIX cDNA in pTRUF5 RSV hF9.3 with the human Factor VIII cDNA sequence. pTRUF5 RSV hF9.2 was digested with HindIII and SstII, and the 3228 bp vector fragment was isolated. SSV9 RSV hF9.3 was digested with HindIII and MluI to yield a 241 bp isolated fragment. SSV9 RSV X.2 was digested with MluI and NcoI to yield a 144 bp isolated fragment. The 3 fragments were ligated to an oligonucleotide linker that contained NcoI and SstII ends, the first 15 nucleotides of the human Factor VIII cDNA sequence and an internal ApaI site (5'CATGGAAATAGAGCT CGGGCCCCCGC3' (SEQ ID NO:1) and 5'GGGGGC CCGAGCTCTATTTC3' (SEQ ID NO:2)).

pTRUF5 RSV hF9.3:

The AAV ITR sequences of SSV9 RSV hF9.3 were replaced with the shorter AAV ITR sequences of pTRUF5. pTRUF5 was digested with BglII to yield a 3167 bp isolated fragment. SSV9 RSV hF9.3 was digested with BglII to yield a 1840 bp isolated fragment. The two pieces were ligated together and clones were selected for those that oriented the promoter region beside the left-hand ITR.

SSV9 RSV hF9.3:

The remaining MMLV LTR and intron sequences in SSV9 RSV hF9.1 were replaced with the human α-globin 2nd intron (McCullough et al., Mol. Cell. Biochem., 17(8): 4562–4571 (1997)). SSV9 RSV hF9.1 was digested with HindIII and BamHI to yield a 5460 bp fragment. SSV9 RSV hF9.1 also was digested with HinPI and BamHI to yield a 1384 bp isolated fragment. pIK6.1RSV was digested with HindIII and XbaI and a 235 bp band containing the RSV promoter was isolated. (pIK6.1RSV was constructed as taught in WO Ser. No. 97/07225 where the known RSV promoter is cloned into the pIK vector.) The 3 fragments were ligated to an oligonucleotide linker that was synthesized in 4 parts with an overlap of 6 bases in the center and SstII and HinPI sites on the ends.

```
#1-5' CTAGTACGCGTAAGGTGAGCGGCGGGCCGGGAGCGATCTGGGTCGAGGGGCGAGA    (SEQ ID NO:3)
TGGCGCCTTCCTCTCAGGGCA3';

#2-5' GAGGATCACGGTGTAGCGCAGGCGGCGGCTGCGGGCCTGGGCCGCACTGACCC      (SEQ ID NO:4)
TCTTCTCTGCACAGCCGCCACCATGCAG3'

#3-5' CGCTGCATGGTGGCGGCTGTGCAGAGAAGAGGGTCAGTGCGGCCCAGGCCCGC      (SEQ ID NO:5)
AGCCGCCGCCTGCGCTACACCGTGATCCTCTGCCCT3';

#4-5' GAGAGGAAGGCGCCATCTCGCCCCTCGACCCAGATCGCTCCCGGCCCGCCGCT      (SEQ ID NO:6)
CACCTTACGCGTA3'
```

To maintain a unique XbaI site in the vector, the oligonucleotide linker truncated the XbaI site into which it went. Additionally, the oligonucleotide linker included an MluI site at the 5' end to aid future cloning steps.

SSV9 RSV hF9.1:

A synthetic poly adenylation sequence was added to SSV9 RSV hF9 intA. The poly A sequence was adapted from Levitt et al. (Genes Develop. 3:1019–1025) and cloned into the vectors as follows. SSV9 RSV hF9 intA was digested with NgoMI and SstII and the 6323 bp fragment was isolated. SSV9 RSV hF9 intA also was digested with NheI and NgoMI and the 736 bp fragment was isolated. An oligonucleotide linker was synthesized in 4 parts with an overlap of 8 bases in the center.

```
                                                (SEQ ID NO:7)
#1-5' GGAATAAAATTTATTTATTTTCATTATT3';
                                                (SEQ ID NO:8)
#2-5' TATGTGTGTTGGTTTTTTGTGTGAGATCTTCTAGAG3';
                                                (SEQ ID NO:9)
#3-5' CTAGCTCTAGAAGATCTCACACAAAAAACCAA3';
                                                (SEQ ID NO:10)
#4,5' CACACATAAATAATGAAAATAAATAAATTTTATTCCGC3'.
```

The SstII and NheI ends of the linker completed the construction.

pAAV-RSV-U-hFVIII:

The vector was made to insert the human factor VIII cDNA sequence into pTRUF5 RSV NSS.2. pTRUF5 RSV NSS.2 was digested with NcoI and SstII and a 3679 bp fragment was isolated. pKS+F8ΔΔcoTGA was digested with NcoI and SstII, a 4376 bp fragment was isolated and the fragments were ligated together.

pTRUF5 RSV NSS.2:

The vector was designed to aid the replacement of the human FIX cDNA in pTRUF5 RSV hF9.2 with the human Factor VIII cDNA sequence. pTRUF5 RSV hF9.2 was digested with HindIII and SstII, and the 3228 bp vector fragment was isolated. SSV9 RSV X.2 was digested with HindIII and NcoI to yield a 451 bp isolated fragment. The 2 fragments were ligated to an oligonucleotide linker that contained NcoI and SstII ends, the first 15 nucleotides of the human Factor VIII cDNA sequence and an internal ApaI site (5'CATGGAAATAGAGCTCGGGCCCCCGC3') (SEQ ID NO:1) and 5'GGGGGCCCGAGCTCTATTTC3' (SEQ ID NO:2)).

pTRUF5 RSV hF9.2:

The AAV ITR sequences of SSV9 RSV hF9.2 were replaced with the shorter AAV ITR sequences of pTRUF5 (Zolotukhin et al., J. Virol., 70:4646–4654). pTRUF5 was digested with BglII to yield a 3167 bp isolated fragment. SSV9 RSV hF9.2 was digested with BglII to yield a 1909 bp isolated fragment. The two pieces were ligated together and clones were selected for those that oriented the promoter region beside the left-hand ITR.

SSV9 RSV hF9.2:

The remaining MMLV LTR and intron sequences in SSV9 RSV hF9.1 were replaced with the human α-globin 2nd intron (McCullough et al., (1997), supra). SSV9 RSV hF9.1 was digested with HindIII and BamHI to yield a 5460 bp isolated fragment. SSV9 RSV hF9.1 also was digested with HinPI and BamHI to yield a 1384 bp isolated fragment. pIK6.1RSV was digested with HindIII and SstII and a 303 bp band containing the RSV promoter and the 5' untranslated region of CMV IE promoter was isolated. The 3 fragments were ligated to an oligonucleotide linker that was synthesized in 4 parts with an overlap of 6 bases in the center and SstII and HinPI sites on the ends.

```
#1-5' ACGCGTAAGGTGAGCGGCGGGCCGGGAGCGATCTGGGTCGAGGGGCGAGATGG       (SEQ ID NO:11)
CGCCTTCCTCTCAGGGCA3'

#2-5' GAGGATCACGGTGTAGCGCAGGCGGCGGCTGCGGGCCTGGGCCGCACTGACCC       (SEQ ID NO:4)
TCTTCTCTGCACAGCCGCCACCATGCAG3'

#3-5' CGCTGCATGGTGGCGGCTGTGCAGAGAAGAGGGTCAGTGCGGCCCAGGCCCGC       (SEQ ID NO:5)
AGCCGCCGCCTGCGCTACACCGTGATCCTCTGCCCT3'

#4-5' GAGAGGAAGGCGCCATCTCGCCCCTCGACCCAGATCGCTCCCGGCCCGCCGCT       (SEQ ID NO:12)
CACCTTACGCGTGC3'
```

To keep a unique SstII site in the vector, the oligonucleotide linker truncated the SstII site into which it went. Additionally, the oligonucleotide linker included an MluI site at the 5' end to aid future cloning steps.

SSV9 RSV hF9 intA:

The vector was developed to delete the bovine growth hormone poly adenylation site from SSV9 RSV hF9 and replace it with an oligonucleotide linker that facilitated cloning of future generations of vectors. The vector SSV9 RSV hF9 was digested with BamHI and SalI, and a 7047 bp fragment was isolated. An oligonucleotide linker, flanked by BamHI and SalI sites, and including internal SstII and NheI sites (5'GATCCCCGCGGCTAGCG3' (SEQ ID NO:13) and 5'TCGACGCTAGCCGCGGG3' (SEQ ID NO:14), was ligated into the vector.

SSV9 RSV hF9:

The vector was constructed to replace the MMLV LTR enhancer/promoter region of pSSV9 MFGS hF9 (Snyder et al., Nature Genetics, 16:270–276) with the RSV enhancer/promoter. The RSV enhancer/promoter from the U3 region of RSV, nucleotides 1–234 (Haseltine et al., PNAS, 74(3):989–993 (1997)), was taken from pRTD43.RSV on a 266 bp HindIII to Asp718 fragment. The MMLV R, U5 and intron were taken from pSSV9 MFGS hF9 on a 1031 bp Asp718 to BglII fragment (Dranoff, PNAS, 90:3539–3543 (1993)). The Factor IX coding sequence, BGH poly A site and both AAV ITR's were taken from pSSV9 MFGS hF9 on a 5969 bp NheI to BglII fragment. The construction was completed with an oligonucleotide linker from NheI to HindIII that included an internal BglII site (5'CTAGCAGATCTA3' (SEQ ID NO:15) and 5'AGCTTAGATCTG3' (SEQ ID NO:16).

SSV9 RSV X.2:

The vector was designed to aid the replacement of the human FIX cDNA in SSV9 RSV hF9.2 with the human Factor VIII cDNA sequence. SSV9 RSV hF9.2 was digested with EcoRI to SstII to remove the FIX cDNA, and the 4274 bp vector fragment was isolated. SSV9 RSV hF9.2 also was digested with EcoRI and NlaIII to yield a 271 bp isolated fragment. The 2 fragments were ligated to an oligonucleotide linker that contained NlaIII and SstII ends and an internal NcoI site (5'GTTATTACCGC 3' (SEQ ID NO:17) and 5'GGTAATAACCATG 3' (SEQ ID NO:18)).

SSV9 RSV NSS.2:

The vector was designed to aid the inclusion of the human Factor VIII cDNA sequence into SSV9 RSV X.2. SSV9 RSV X.2 was digested with NcoI and SstII to yield a 4544 bp isolated fragment. An oligonucleotide linker that contained NcoI and SstII ends, the first 15 nucleotides of the human Factor VIII cDNA sequence and an internal ApaI site (5'CATGGAAATAGAGCTCGG GCCCCCGC3' (SEQ ID NO:1) and 5'GGGGGCC CGAGCTCTATTTC3' (SEQ ID NO:2) was ligated into the vector.

pAAV-FIX-hFVIII:

The RSV promoter in pAAV-RSV-hFVIII was replaced with the human factor IX promoter from the pSVSPORT FIX po vector.

pAAV-FIX-U-hFVIII:

The RSV promoter in pAAV-RSV-U-hFVIII was replaced with the human factor IX promoter from the pSVSPORT FIX po vector.

pSVSPORT FIX po:

PCR primers were designed to amplify sequences from −220 to +20 relative to the FIX transcription initiation site (Salier et al., JBC, 265 (12) :7062–7068 (1990)). The template used to amplify the promoter sequences was a bacterial artificial chromosome, B88, that encoded the entire FIX gene on a 40 kb cassette. The forward primer sequence was 5'GGGAAGCTTCA-GACTAACTGGACCACTCAT3' (SEQ ID NO:19). The reverse primer sequence was 5'GGGACGCGTG-GTGATTATTAAATTTCACCTC3' (SEQ ID NO:20). The forward primer was engineered to include a HindIII site at the 5' end of the promoter, and the reverse primer was engineering to include an MluI site at the 3' end of the promoter. Additionally, the reverse primer mutated the 'G' nucleotide at position +18 to 'C' to remove an open reading frame in the FIX (Factor IX) 5' untranslated region. After PCR amplification, the product was digested with HindIII and MluI and electrophoresed. The 252 bp FIX promoter fragment was isolated and ligated into the 3150 bp, HindIII and MluI digested, shuttle vector pSVSPORT (Gibco/BRL).

pKS$^+$F8ΔΔNcoTGA is a vector that contains an SQ B domain deletion (Lind et al., Eur. J. Biochem., 232:19–27 (1995)) human Factor VIII cDNA in which the sequence surrounding the initiator methionine has been altered to enhance efficient translation (Kozak, J. Mol. Biol., 196:947–950 (1987)), the Gln at position 2 of the leader sequence has been changed to Glu and untranslated sequences 3' of the translation stop codon have been removed. pKS$^+$F8ΔΔNcoTGA was generated by ligating a 1.8 kb NgoMI-PflMI fragment from pKS$^+$F83'SQ with a 3 kb SacI-PflMI fragment from pKS$^+$F8ΔSQΔintron and a 2.5 kb SacI-NgoMI fragment from pKS$^{+\ NcoInt}$.

pKS$^+$F83'SQ was generated by ligating a 755 bp HindIII-PflMI fragment from pKS$^+$F8ΔSQ with a 1.2 kb PflMI-XbaI fragment from pKS$^+$F8 and a 3 kb XbaI-HindIII fragment from pKS$^+$3'F8.

pKS$^+$F8ΔSQΔintron was generated by ligating a 1.35 kb BglII-PflMI fragment from pKS$^+$F8ΔSQ with 7.1 kb PflMI-BglII fragment from pKS$^+$F8Δintron.

pKS$^+$NcoInt encodes the first four amino acids of F8 so that the ATG is contained in an NcoI site and changes the Gln at position 2 of the leader sequence to Glu. pKS$^+$NcoInt was generated by inserting an XhoI-SacI linker consisting of synthetic oligos 5'-TCGAGCCATGGAAATAGAGCT-3' (SEQ ID NO:21) and 5'-CTATTTCCATGGA-3' (SEQ ID NO:22) into pKS+ digested with XhoI and SacI.

To generate pKS$^+$F8ΔSQ, sequence coding for amino acids Gln 744 to Ser 1637 (Lind et al., (1995), supra) were deleted by loop-out mutagenesis using pKS+F8 as the template and oligonucleotide 5'-AGCTTCTCCAGA ATCCACCAGTCTTGAAA-3' (SEQ ID NO:23) as the primer to generate pKS$^+$F8ΔSQ.

pKS$^+$F8Δintron was generated by replacing the 638 bp SacI-AflII fragment of pKS$^+$F8 containing a truncated F8 intron with a 309 bp SacI-AflII fragment generated by PCR using human liver cDNA (Clontech) as a template with primer 5'-CCATGGATGCAAATAGAGCTCTCCACC-3' (SEQ ID NO:24) and primer 5'-TCCAGTAGGATA CACCAACAGC-3' (SEQ ID NO:25), followed by digestion with SacI and AflII.

pKS$^+$3'F8, which contains the 3' 105 bp coding sequences of FVIII followed by an introduced SacII site, was generated by inserting a 113 bp SacII-XbaI fragment (generated by PCR using pKS$^+$F8 as the template with oligonucleotide primer 5'-AGACTCCTTCACACCTGTGGT-3' (SEQ ID NO:26) and oligo primer 5'-GAATTCCCGCGGT CAGTAGAGGTCCTGTGCCT-3' (SEQ ID NO:27), followed by digestion with SacII and XbaI) into the 2.9 kb XbaI-SacII fragment of pKS$^+$.

pKS$^+$F8 was generated by inserting a 5 kb SacI-SalI fragment from pUC19AdRSVF8 (Richard Morgan, National Institutes of Health, Clinical Gene Therapy Branch) into the 2.9 kb SacI-SalI fragment from pKS$^+$ (Stratagene).

Example 2 rAAV Vector Production

The recombinant AAV vectors were packaging as described by Snyder et al., "Production of recombinant adeno-associated viral vectors," in Current Protocols in Human Genetics, pp. 12.1.1–12.1.24, N. Dracopoli et al., eds. (John Wiley & Sons, New York, 1996) with modifications. Briefly, subconfluent 293 cells were cotransfected with the vector plasmid and the AAV helper plasmid pUC19.ACG was used to supply AAV rep and cap functions. The pUC19.ACG construct harbors and XbaI fragment of pACG2-1 described by Li et al. [J. Virol., 71:7236–5243 (1997)] which was isolated by PCR to change the 5' XbaI site to HindIII and the 3' XbaI site to BamHI. The fragment was inserted into the HindIII and the BamHI sites in pUC-19, and does not harbor the adenoviral terminal repeats. Cells then were infected with adenovirus Ad5dl312 (an E1A mutant) at an m.o.i. of 2 and the infection was allowed to proceed for 72 hours. Cells were harvested and three freeze/thaw cycles were carried out to lyse the cells. The nucleic acid in the lysate was digested with 250 U/ml Benzonase (Nycomed) at 37° C. for 10 minutes and then centrifuged 1500 g to pellet the cellular debris. The cell lysate then was fractionated by ammonium sulfate precipitation and the rAAV virions were purified on two sequential iospycnic CsCl gradients formed in a Beckman NVT65 rotor at 60,000 rpm for 6 hours minimum each. Fractions were collected using a Beckman Fraction Recovery System (#343890). Following CsCl banding, the fractions containing rAAV were dialyzed against PBS (JRH Biosciences, #5930078P). The samples then were heated for 45 minutes at 56° C. and stored at −80° C.

Example 3

Viral Infections 293 cells were seeded at a total of $1 \times 10^6$ cell per well of a six-well tissue culture plate and incubated overnight at 37° C. The medium was removed from the wells and replaced with IMDM containing 10% heat-inactivated fetal bovine serum, 1% antibiotic/antimycotic solution with 10 mM $MgCl_2$, and then the plates were returned to the incubator for 1–2 hours. Cells were infected with rAAV by adding the virus directly to the tissue culture media. Typically, a dose of $1 \times 10^{10}$ particles per $1 \times 10^6$ seeded cells yields detectable levels of human factor VIII. Cells were co-infected with Ad5 d1309 at an MOI of 2 and then incubated at 37° C. After 48 hours, the cell culture media was removed from the tissue culture plate and analyzed for human factor VIII activity.

Example 4

Plasmid Transfection 293 cells were seeded into 10 cm dishes at $4.5 \times 10^6$ cells/dish and transfected 24 hours later by the calcium phosphate method (Snyder, (1996), supra). Ten µg of either pMFGΔBVIII (Dwarki et al. PNAS 92:1023–1027), pAAV-RSV-U-hFVIII and pAAV-RSV-hFVIII vectors were used in the transfection. After 5 hours the media were changed to 7.5 mls IMDM+10% heat inactivated FBS+20 mM $MgCl_2$. Supernatants were collected after 48 hours for ELISA and FVIII activity assays.

Example 5

FVIII Determination

FVIII function was determined by a chromogenic assay that measures FVIII dependent generation of factor Xa from factor X (Carlebjork et al., Throm. Res., 47:5–14 (1987); Rosen, Scand. J. Haemot. Suppl., 40:139–145 (1984)) using a commercially available kit (Coatest, Kabivitrum, Stockholm).

FVIII was quantified in a ELISA using commercially available reagents, such as mAb's directed to the H chain or to the L chain, and suitable reporter reagents practicing known methods.

Factor VIII activity was observed.

All references mentioned in the instant specification are herein incorporated by reference.

The invention now being fully described, it will be apparent to one of ordinary skill in the art that many changes and modifications can be made thereto without departing from the spirit or scope of the appended claims.

What is claimed is:

1. A recombinant adeno-associated virus (rAAV) vector for obtaining Factor VIII activity, comprising, in operable linkage:
   (a) a first inverted terminal repeat;
   (b) an intervening sequence or splice donor/acceptor site;
   (c) a promoter;
   (d) a polynucleotide encoding a Factor VIII polypeptide, wherein the amino acids between the Thrombin 740 and Furin 1648 proteolytic cleavage sites are deleted;
   (e) a polyadenylation site; and
   (f) a second inverted terminal repeat;
wherein said vector is packageable in an adeno-associated virus (AAV) particle and expresses Factor VIII activity.

2. The vector of claim 1, wherein said promoter is a liver-specific promoter.

3. The vector of claim 1, wherein said promoter is obtained from a virus.

4. The vector of claim 3, wherein said virus is Rous sarcoma virus (RSV).

5. The vector of claim 1, wherein said polypeptide consists of two Factor VIII heavy chain A domains, and a Factor VIII light chain A domain and two Factor VIII C domains.

6. The vector of claim 1, wherein said splice donor/acceptor site is between said promoter (c) and said polynucleotide (d).

7. The vector of claim 1, wherein said splice donor/acceptor site is obtained from human α-globin.

8. The vector of claim 1, further comprising an untranslated region.

9. The vector of claim 8, wherein said untranslated region is a cytomegalovirus untranslated region.

10. The vector of claim 9, wherein said cytomegalovirus untranslated region is between said promoter (c) and said polynucleotide (d).

11. The vector of claim 1, which is pAAV-RSV-hFVIII.

12. The vector of claim 1, which is pAAV-RSV-U-hFVIII.

13. The vector of claim 1, wherein said promoter is less than about 800 bp.

14. The vector of claim 13, wherein said promoter is about 250 bp.

15. The vector of claim 14, wherein said promoter is the RSV promoter.

16. The vector of claim 1, comprising modification of the initiation codon of said polynucleotide (d) to enhance expression of said polypeptide.

17. The vector of claim 1, wherein said promoter is the Factor IX promoter.

18. The vector of claim 17, which is pAAV-FIX-hFVIII.

19. The vector of claim 17, which is pAAV-FIX-U-hFVIII.

20. A virus particle containing the vector of claim 1.

* * * * *

SEQUENCE LISTING

<160> NUMBER OF SEQ ID NOS: 27

<210> SEQ ID NO 1
<211> LENGTH: 26
<212> TYPE: DNA
<213> ORGANISM: Homo sapiens

<400> SEQUENCE: 1
catggaaata gagctcgggc ccccgc                                          26

<210> SEQ ID NO 2
<211> LENGTH: 20
<212> TYPE: DNA
<213> ORGANISM: Homo sapiens

<400> SEQUENCE: 2
gggggcccga gctctatttc                                                 20

<210> SEQ ID NO 3
<211> LENGTH: 76

```
<212> TYPE: DNA
<213> ORGANISM: Artificial Sequence
<220> FEATURE:
<223> OTHER INFORMATION: Description of Artificial Sequence:
      oligonucleotide linker

<400> SEQUENCE: 3
ctagtacgcg taaggtgagc ggcgggccgg gagcgatctg ggtcgagggg cgagatggcg    60
ccttcctctc agggca                                                    76

<210> SEQ ID NO 4
<211> LENGTH: 81
<212> TYPE: DNA
<213> ORGANISM: Artificial Sequence
<220> FEATURE:
<223> OTHER INFORMATION: Description of Artificial Sequence:
      oligonucleotide linker

<400> SEQUENCE: 4
gaggatcacg gtgtagcgca ggcggcggct gcgggcctgg gccgcactga ccctcttctc    60
tgcacagccg ccaccatgca g                                              81

<210> SEQ ID NO 5
<211> LENGTH: 89
<212> TYPE: DNA
<213> ORGANISM: Artificial Sequence
<220> FEATURE:
<223> OTHER INFORMATION: Description of Artificial Sequence:
      oligonucleotide linker

<400> SEQUENCE: 5
cgctgcatgg tggcggctgt gcagagaaga gggtcagtgc ggcccaggcc cgcagccgcc    60
gcctgcgcta caccgtgatc ctctgccct                                      89

<210> SEQ ID NO 6
<211> LENGTH: 66
<212> TYPE: DNA
<213> ORGANISM: Artificial Sequence
<220> FEATURE:
<223> OTHER INFORMATION: Description of Artificial Sequence:
      oligonucleotide linker

<400> SEQUENCE: 6
gagaggaagg cgccatctcg cccctcgacc cagatcgctc ccggcccgcc gctcacctta    60
cgcgta                                                               66

<210> SEQ ID NO 7
<211> LENGTH: 28
<212> TYPE: DNA
<213> ORGANISM: Artificial Sequence
<220> FEATURE:
<223> OTHER INFORMATION: Description of Artificial Sequence:
      oligonucleotide linker

<400> SEQUENCE: 7
ggaataaaat ttatttattt tcattatt                                       28

<210> SEQ ID NO 8
<211> LENGTH: 36
<212> TYPE: DNA
<213> ORGANISM: Artificial Sequence
<220> FEATURE:
<223> OTHER INFORMATION: Description of Artificial Sequence:
      oligonucleotide linker
```

```
<400> SEQUENCE: 8
tatgtgtgtt ggttttttgt gtgagatctt ctagag                                  36

<210> SEQ ID NO 9
<211> LENGTH: 32
<212> TYPE: DNA
<213> ORGANISM: Artificial Sequence
<220> FEATURE:
<223> OTHER INFORMATION: Description of Artificial Sequence:
      oligonucleotide linker

<400> SEQUENCE: 9
ctagctctag aagatctcac acaaaaaacc aa                                      32

<210> SEQ ID NO 10
<211> LENGTH: 38
<212> TYPE: DNA
<213> ORGANISM: Artificial Sequence
<220> FEATURE:
<223> OTHER INFORMATION: Description of Artificial Sequence:
      oligonucleotide linker

<400> SEQUENCE: 10
cacacataaa taatgaaaat aaataaattt tattccgc                                38

<210> SEQ ID NO 11
<211> LENGTH: 71
<212> TYPE: DNA
<213> ORGANISM: Artificial Sequence
<220> FEATURE:
<223> OTHER INFORMATION: Description of Artificial Sequence:
      oligonucleotide linker

<400> SEQUENCE: 11
acgcgtaagg tgagcggcgg gccgggagcg atctgggtcg aggggcgaga tggcgccttc        60
ctctcagggc a                                                             71

<210> SEQ ID NO 12
<211> LENGTH: 67
<212> TYPE: DNA
<213> ORGANISM: Artificial Sequence
<220> FEATURE:
<223> OTHER INFORMATION: Description of Artificial Sequence:
      oligonucleotide linker

<400> SEQUENCE: 12
gagaggaagg cgccatctcg ccctcgacc cagatcgctc ccggcccgcc gctcaccta          60 cgcgtgc                                                                  67

<210> SEQ ID NO 13
<211> LENGTH: 17
<212> TYPE: DNA
<213> ORGANISM: Artificial Sequence
<220> FEATURE:
<223> OTHER INFORMATION: Description of Artificial Sequence:
      oligonucleotide linker

<400> SEQUENCE: 13
gatccccgcg gctagcg                                                       17

<210> SEQ ID NO 14
<211> LENGTH: 17
<212> TYPE: DNA
<213> ORGANISM: Artificial Sequence
<220> FEATURE:
```

```
<223> OTHER INFORMATION: Description of Artificial Sequence:
      oligonucleotide linker

<400> SEQUENCE: 14
tcgacgctag ccgcggg                                                    17

<210> SEQ ID NO 15
<211> LENGTH: 12
<212> TYPE: DNA
<213> ORGANISM: Artificial Sequence
<220> FEATURE:
<223> OTHER INFORMATION: Description of Artificial Sequence:
      oligonucleotide linker

<400> SEQUENCE: 15
ctagcagatc ta                                                         12

<210> SEQ ID NO 16
<211> LENGTH: 12
<212> TYPE: DNA
<213> ORGANISM: Artificial Sequence
<220> FEATURE:
<223> OTHER INFORMATION: Description of Artificial Sequence:
      oligonucleotide linker

<400> SEQUENCE: 16
agcttagatc tg                                                         12

<210> SEQ ID NO 17
<211> LENGTH: 11
<212> TYPE: DNA
<213> ORGANISM: Artificial Sequence
<220> FEATURE:
<223> OTHER INFORMATION: Description of Artificial Sequence:
      oligonucleotide linker

<400> SEQUENCE: 17
gttattaccg c                                                          11

<210> SEQ ID NO 18
<211> LENGTH: 13
<212> TYPE: DNA
<213> ORGANISM: Artificial Sequence
<220> FEATURE:
<223> OTHER INFORMATION: Description of Artificial Sequence:
      oligonucleotide linker

<400> SEQUENCE: 18
ggtaataacc atg                                                        13

<210> SEQ ID NO 19
<211> LENGTH: 30
<212> TYPE: DNA
<213> ORGANISM: Artificial Sequence
<220> FEATURE:
<223> OTHER INFORMATION: Description of Artificial Sequence: primer

<400> SEQUENCE: 19
gggaagcttc agactaactg gaccactcat                                      30

<210> SEQ ID NO 20
<211> LENGTH: 31
<212> TYPE: DNA
<213> ORGANISM: Artificial Sequence
<220> FEATURE:
<223> OTHER INFORMATION: Description of Artificial Sequence: primer
```

```
<400> SEQUENCE: 20
gggacgcgtg gtgattatta aatttcacct c                              31

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 21
tcgagccatg gaaatagagc t                                         21

<210> SEQ ID NO 22
<211> LENGTH: 13
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 22
ctatttccat gga                                                  13

<210> SEQ ID NO 23
<211> LENGTH: 30
<212> TYPE: DNA
<213> ORGANISM: Artificial Sequence
<220> FEATURE:
<223> OTHER INFORMATION: Description of Artificial Sequence: primer

<400> SEQUENCE: 23
agcttctccc agaatccacc agtcttgaaa                                30

<210> SEQ ID NO 24
<211> LENGTH: 27
<212> TYPE: DNA
<213> ORGANISM: Artificial Sequence
<220> FEATURE:
<223> OTHER INFORMATION: Description of Artificial Sequence: primer

<400> SEQUENCE: 24
ccatggatgc aaatagagct ctccacc                                   27

<210> SEQ ID NO 25
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 25
tccagtagga tacaccaaca gc                                        22

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 26
agactccttc acacctgtgg t                                         21
```

```
<210> SEQ ID NO 27
<211> LENGTH: 32
<212> TYPE: DNA
<213> ORGANISM: Artificial Sequence
<220> FEATURE:
<223> OTHER INFORMATION: Description of Artificial Sequence: primer

<400> SEQUENCE: 27
gaattcccgc ggtcagtaga ggtcctgtgc ct                                32
```